US012306180B2

(12) United States Patent
Carreira et al.

(10) Patent No.: US 12,306,180 B2
(45) Date of Patent: *May 20, 2025

(54) TRI-FUNCTIONAL CROSSLINKING REAGENTS

(71) Applicant: ETH Zurich, Zurich (CH)

(72) Inventors: Erick Moran Carreira, Zumikon (CH); Michael Andreas Schafroth, Zurich (CH); Nadine Sobotzki, Zurich (CH); Bernd Wollscheid, Zurich (CH)

(73) Assignee: ETH Zurich, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/860,287

(22) Filed: Jul. 8, 2022

(65) Prior Publication Data
US 2022/0373541 A1 Nov. 24, 2022

Related U.S. Application Data

(63) Continuation of application No. 15/774,275, filed as application No. PCT/EP2016/077122 on Nov. 9, 2016, now Pat. No. 11,385,225.

(30) Foreign Application Priority Data

Nov. 10, 2015 (EP) ..................................... 15003213

(51) Int. Cl.
G01N 33/68 (2006.01)
C07D 207/50 (2006.01)
(Continued)

(52) U.S. Cl.
CPC ..... *G01N 33/54353* (2013.01); *C07D 207/50* (2013.01); *C07D 213/81* (2013.01);
(Continued)

(58) Field of Classification Search
CPC ......... G01N 33/54353; G01N 2400/00; G01N 33/566; G01N 33/6845; C07D 207/50;
(Continued)

(56) References Cited

U.S. PATENT DOCUMENTS 9,766,235 B2    9/2017  Frei et al.
11,385,225 B2 * 7/2022  Carreira ........... C08G 65/33337
(Continued)

FOREIGN PATENT DOCUMENTS

WO    2012/104051 A1    8/2012

OTHER PUBLICATIONS

Crisalli, P. et al. "Water-Soluble Organocatalysts for Hydrazone and Oxime Formation" The Journal of Organic Chemistry, 2013, pp. 1184-1189, vol. 78.

*Primary Examiner* — Shafiqul Haq
*Assistant Examiner* — Nam P Nguyen
(74) *Attorney, Agent, or Firm* — Anderson Patent Law Firm LLC

(57) ABSTRACT

The present invention relates to tri-functional crosslinking reagents carrying (i) a ligand-reactive group for conjugation to a ligand of interest having at least one binding site on a target glycoprotein receptor, (ii) a hydrazone group for the capturing of oxidized receptor-glycoproteins and (iii) an affinity group selected from azides and aklynes for the detection, isolation and purification of captured glycoproteins; as well as their manufacturing. The invention further provides for improved methods of detecting, identifying and characterizing interactions between ligands and their corresponding target glycoproteins on living cells and in biological fluids. The invention further provides for new uses of catalysts in such methods.

12 Claims, 3 Drawing Sheets

Figure 1:
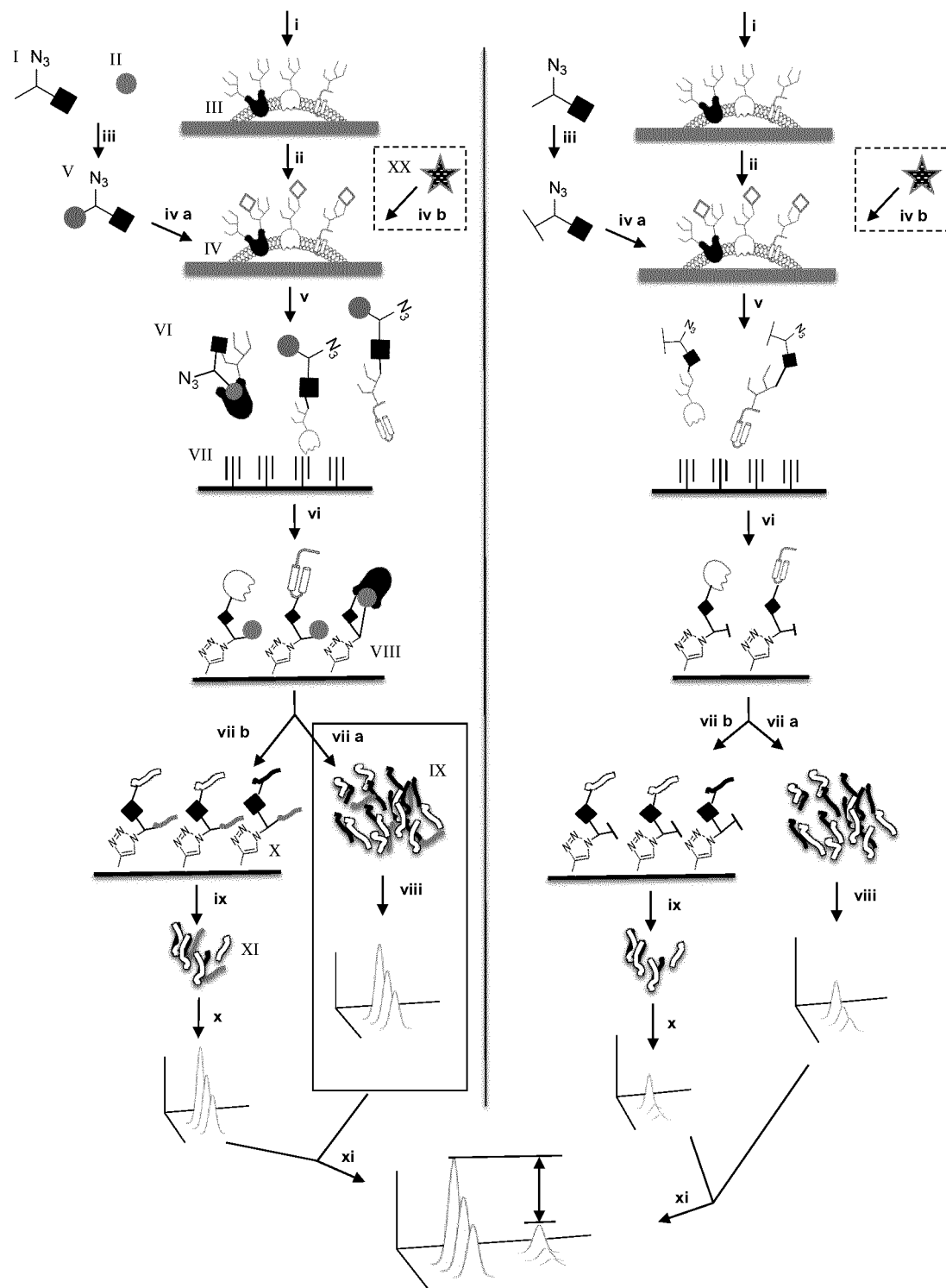

(51) Int. Cl.
*C07D 213/81* (2006.01)
*C07D 401/12* (2006.01)
*C08G 65/325* (2006.01)
*C08G 65/333* (2006.01)
*G01N 33/543* (2006.01)
*G01N 33/566* (2006.01)

(52) U.S. Cl.
CPC ......... *C07D 401/12* (2013.01); *C08G 65/325* (2013.01); *C08G 65/33337* (2013.01); *G01N 2400/00* (2013.01)

(58) Field of Classification Search
CPC .. C07D 213/81; C07D 401/12; C08G 65/325; C08G 65/33337
See application file for complete search history.

(56) References Cited

U.S. PATENT DOCUMENTS

| | | |
|---|---|---|
| 2011/0207171 A1 | 8/2011 | Agnew et al. |
| 2014/0011212 A1 | 1/2014 | Frei et al. |

* cited by examiner

TRI-FUNCTIONAL CROSSLINKING REAGENTS

The present invention relates to tri-functional crosslinking reagents carrying (i) a ligand-reactive group for conjugation to a ligand of interest having at least one binding site on a target glycoprotein, (ii) a hydrazone group for the capturing of oxidized or aldehyde containing receptor-glycoproteins (iii) an affinity group for the detection, isolation and purification of captured glycoproteins, their methods of production, as well as their use in methods for detecting, identifying and characterizing interactions between ligands and their corresponding glycoprotein target receptors on living cells and in biological fluids.

Glycosylation is one of the most prominent protein modifications and many if not most secretory and membrane-bound proteins produced by mammalian cells contain covalently linked glycans. In the assembly of complex organisms such oligosaccharide portions serve a variety of structural and functional roles for the folding, subcellular localization, turnover, activity and interactions of secreted and cell surface proteins.

Secreted glycoproteins include e.g. cytokines, hormones, growth and differentiation factors, enzymes, neuropeptides, vasomediators, antigen recognition molecules, immunoregulatory molecules, structural glycoproteins, and other bioactive molecules. Those proteins are important in many recognition events, such as cell-to-cell signaling, immune responses, apoptosis, host-pathogen interactions and the pathogenesis of many diseases. Thereby, the specificity of such glycoproteins for certain target receptors is essential in regulating cell-to-cell communication. Thus the identification and characterization of ligand binding interactions of secreted glycoproteins with their targets is essential for a molecular understanding of biological information transfer.

In analogy, the engagement of cell surface glycoprotein receptors (CSRs) by ligands, such as proteins, peptides, hormones, chemical molecules, pharmaceutical drugs or toxins enables the transfer of information from the cellular microenvironment into the cell. Despite the fact that this cell surface signaling gateway is critical for cellular responses, the receptors for many functional ligands remain unknown. This is mainly due to technological limitations in the identification of hydrophobic membrane receptor proteins and due to transient, low affinity interactions of ligands with their corresponding CSRs. Therefore, many signaling proteins and molecules remain orphan ligands without a known primary molecular target—invaluable information currently missing for a detailed molecular understanding of the respective mechanisms of signal transduction, drug action, off-target effects or disease-associated signaling networks.

EP2670755 discloses specific tri-functional crosslinking reagents and methods to identify the interaction between an (orphan) ligand and a glycoprotein target receptor. Although the therein disclosed compound and workflow is suitable for the successful identification of ligand-receptor interactions, the compound, as well as the associated sample processing workflow have certain constraints: First, the method disclosed therein is limited to a pH of 6.5 or even more acidic. This could be problematic in cases where the ligand-receptor interactions is impaired if the pH is not physiological. Second, the identification of the target receptor is based exclusively on N-glycosylated peptides of the target. Receiving information about un-glycosylated peptides of the glycoprotein target receptor would enable also the identification of other target receptors that are not N-glycosylated; it would provide information about the precise proteoform of the target receptors and overall enable a more reliable quantification of target receptor candidates.

This highlights the need for an improved method to determine the interaction between ligands and target glycoprotein receptors and the need to provide new compounds suited to such methods.

The current invention overcomes the limitations discussed above largely through the compounds and methods as described herein. Further aspects of the invention are disclosed in the specification and independent claims, preferred embodiments are disclosed in the specification and the dependent claims.

The present invention will be described in more detail below. It is understood that the various embodiments, preferences and ranges as provided/disclosed in this specification may be combined at will. Further, depending of the specific embodiment, selected definitions, embodiments or ranges may not apply.

In a first aspect, the invention relates to the present invention is directed towards tri-functional crosslinking reagents of formula (I)

In a second aspect, the invention relates to the use of the crosslinking reagents of the invention for characterizing and analyzing ligand-target glycoprotein receptor interactions In a third aspect, the invention relates methods of identifying specific interactions between a ligand and a target glycoprotein receptor having at least one carbohydrate residue in a sample.

In a fourth aspect, the invention relates to the use of specific organic compounds as non-toxic catalysts in biochemical reactions on living cells, particularly in the methods described herein (3rd aspect)

In a fifth aspect, the invention relates to a kit comprising a crosslinking reagent as described herein (1st aspect) and optionally an organic compound as described herein (4th aspect).

For a more detailed understanding the present invention is visualized in the following figures.

FIG. 1: provides a schematic illustration of the ligand-based receptor capturing (LRC-) workflow of cell surface target glycoprotein receptors. This figure specifically illustrates the various aspects of this invention and particularly the steps outlined in the third aspect of this invention. In this figure, the chemical entities (I) to (XX) and the method steps (i) to (xi) are schematically shown; left: workflow; right: control experiment. This figure outlines the invention for the embodiment where A=azide.

Figure 2:
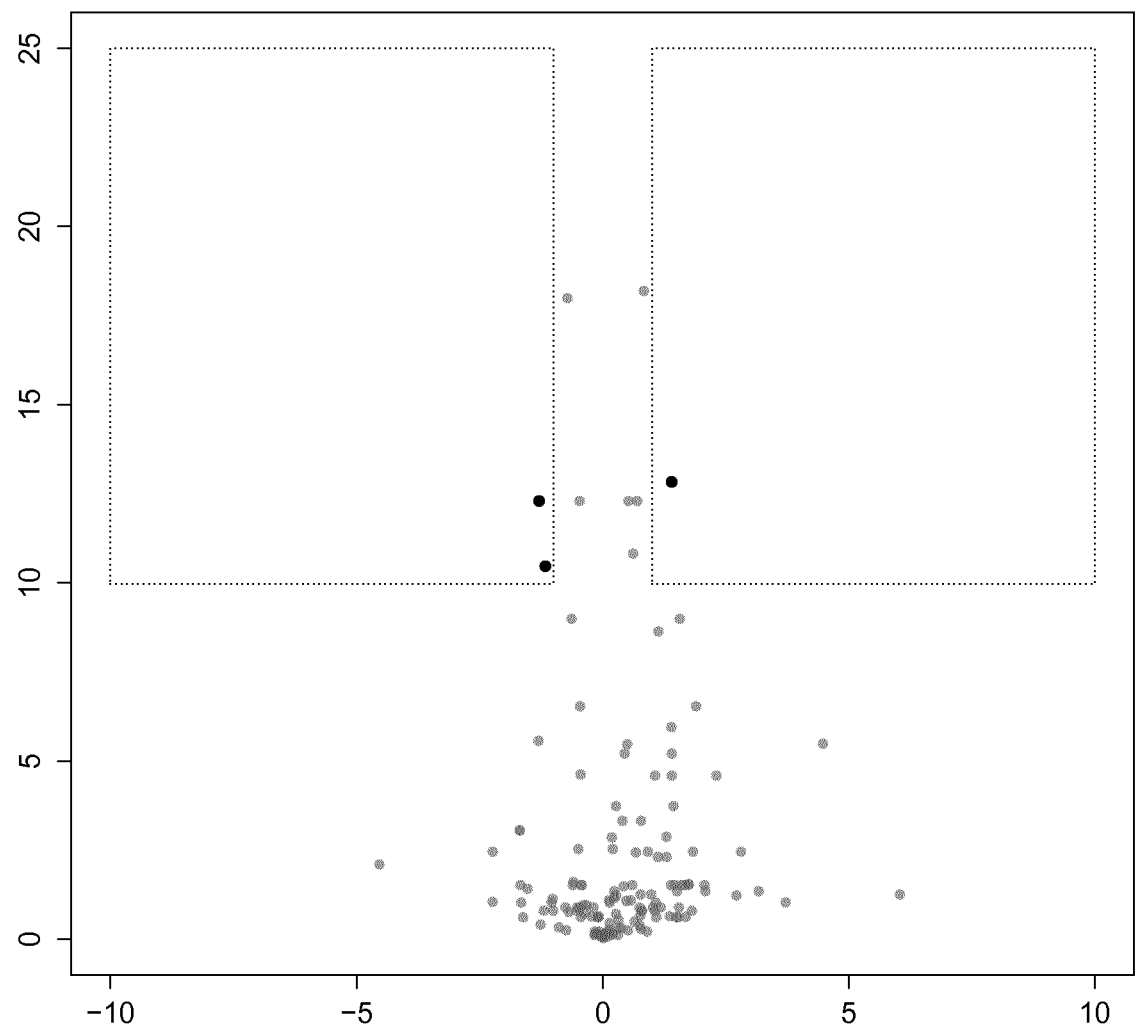

FIG. 2: shows the relative-quantitative evaluation of ligand-based receptor capturing with the model ligand epidermal growth factor (EGF) at pH7.4. The receptor capture was performed with an EGF-HATRIC conjugate on H358 bronchiole cell line. The plot shows the negative log2-transformed false-discovery rate (FDR) adjusted p-values on the y-axis versus log2-transformed fold changes of the ratio EGF/control on the x-axis. All proteins that were quantified throughout the two conditions are displayed as dots. The glycoprotein target receptor candidates are defined as receptors with an FDR-adjusted p-value less than or equal to 0.001 and an enrichment factor of fourfold or greater. The upper left corner defines glycoprotein target receptors candidates in the control and the upper right box defines glycoprotein target receptor candidates of the ligand of interest, i. e. EGF. Glycoprotein target receptor candidates that were identified are displayed as black dots. The known glycoprotein target receptor epidermal growth factor receptor (EGFR) was identified in the upper right target box as the target receptor for EGF.

Figure 3:
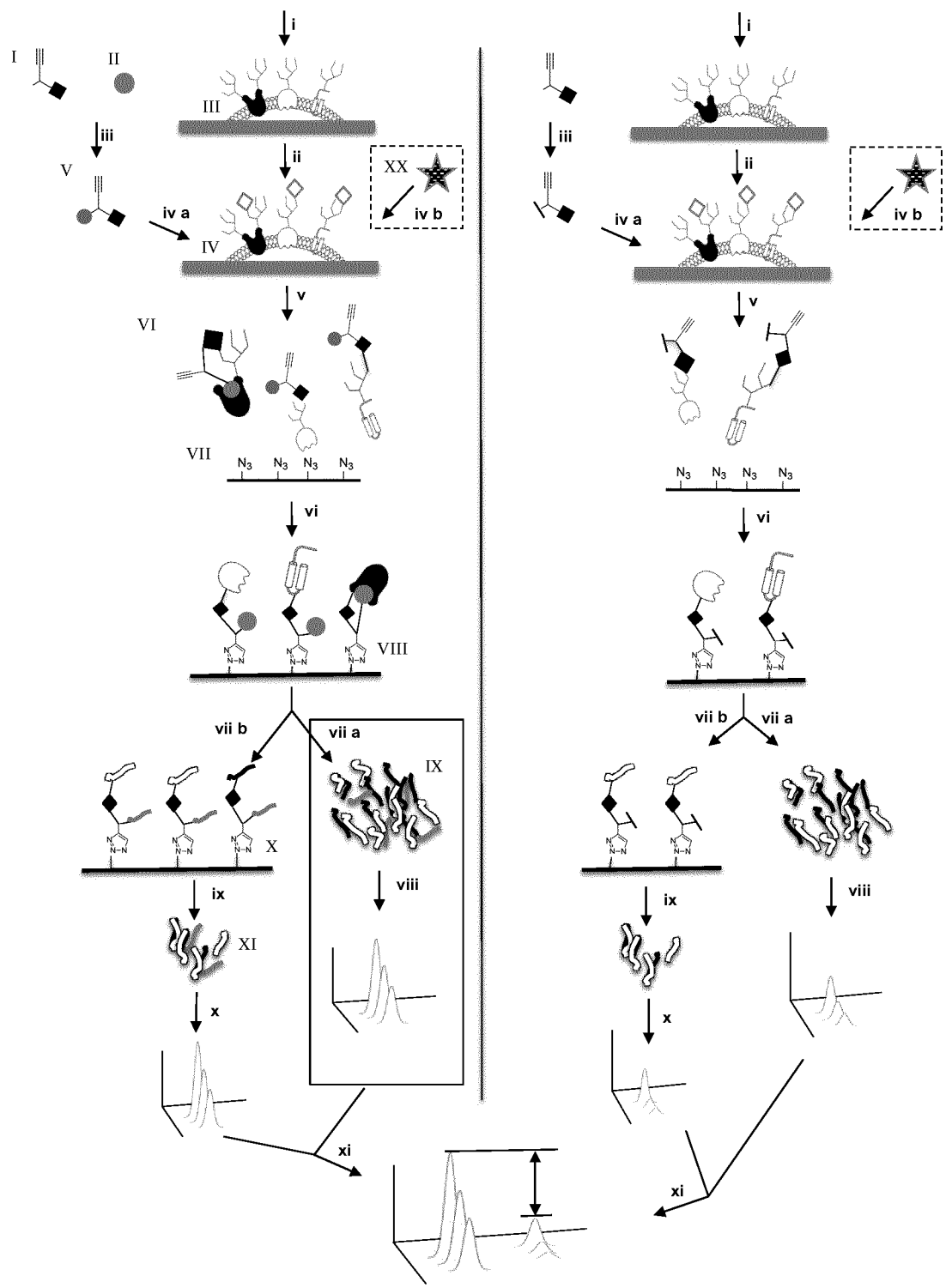

FIG. 3: provides a schematic illustration of an alternative LRC-workflow and complements FIG. 1 for the embodiment A=alkyne.

Unless defined otherwise, the following definitions are used throughout the description:

As used herein, the term "a," "an," "the" and similar terms used in the context of the present invention (especially in the context of the claims) are to be construed to cover both the singular and plural unless otherwise indicated herein or clearly contradicted by the context. The term "plurality" refers to a number of two or more.

As used herein, the terms "including", "containing" and "comprising" are used herein in their open, non-limiting sense. The term "tri-functional" means "carrying three functionalities". Thus a tri-functional (crosslinking) reagent refers to a (crosslinking) reagent having three functionalities. The term "heterotri-functional" means "carrying three different functionalities".

The term "alkyl" as used herein refers to a straight or branched hydrocarbon containing 1-24, preferably 1 to 12 carbon atoms. Examples of alkyl groups include, but are not limited to, methyl, ethyl, n-propyl, i-propyl, n-butyl, i-butyl, and t-butyl, pentyl, hexyl. The term "alkoxy" refers to an —O-alkyl group.

The term "alkylene", also termed "alkandiyl", as used herein refers to a divalent radical derived from a hydrocarbon, for example —CHR—(CHR)$_n$— with R being H or a substituent of choice. Typically, an alkylene group will have from 1 to 24 carbon atoms (i.e. n=24), preferably 10 to 24 carbon atoms. The term "heteroalkylene" as used herein refers to an alkylene having one or more heteroatoms, such as O, N or S, preferably O or N, inserted into the alkylradicals.

The term "cycloalkyl" refers to a saturated and partially unsaturated cyclic hydrocarbon group having 3 to 12 carbons. Examples of cycloalkyl groups include, but are not limited to, cyclopropyl, cyclobutyl, cyclopentyl, cyclopentenyl, cyclohexyl, cyclohexenyl, cycloheptyl, and cyclooctyl.

The term "heterocycloalkyl" refers to a nonaromatic 5-8 membered monocyclic, 8-12 membered bicyclic, or 11-14 membered tricyclic ring system having one or more heteroatoms (such as O, N, or S). Examples of heterocycloalkyl groups include, but are not limited to, piperazinyl, pyrrolidinyl, dioxanyl, morpholinyl, and tetrahydrofuranyl, glucosyl.

The term "aryl" as used herein refers to a 6-carbon monocyclic, 10-carbon bicyclic, 14-carbon tricyclic aromatic ring system wherein each ring may have unsubstituted or 1 to 4 substituents.

Examples of aryl groups include, but are not limited to, phenyl, naphthyl, and anthracenyl. Phenylene, as used in the context of the present invention, preferably denotes a 1,2-, 1,3- or 1,4-phenylene group, which is optionally substituted.

The term "heteroaryl" refers to an aromatic 5-8 membered monocyclic, 8-12 membered bicyclic, or 11-14 membered tricyclic ring system having one or more heteroatoms (such as O, N, or S). Examples of heteroaryl groups include pyridyl, furyl, imidazolyl, benzimidazolyl, pyrimidinyl, thienyl, quinolinyl, indolyl, and thiazolyl. Pyridyl includes 2-pyridyl, 3-pyridyl and 4-pyridyl, preferably 2-pyridyl. The term "heteroaralkyl" refers to an alkyl group substituted with a heteroaryl group.

The term "optionally substituted" as used herein includes unsubstituted and substituted. Such optional substituents being preferably selected from the group consisting of Hal, —OR, —CN, —NO$_2$, —COOR, C(1-8)alkyl, C(1-8)alkylene, and C(1-8)alkoxy, wherein R is from 1 to 8 carbon atoms.

Further, the groups Cycloalkyl, heterocycloalkyl, aryl, heteroaryl may be optionally substituted by 1 to 4 substitutents. Examples of substituents include, but are not limited to, at least one halo, hydroxyl, amino, cyano, nitro, mercapto, carboxy, or a hydrocarbyl group selected from an alkyl, alkenyl, alkylamino, dialkylamino, or alkoxy group having one to six carbon atoms.

Exemplary hydrocarbyl-substituted cycloalkyl groups include 2-methylcyclopropyl, 2-ethylcyclopropyl, 2-methylcyclobutyl, 3-methylcyclobutyl, 2-methylcyclopentyl, 2,3-dimethylcyclopentyl, 3-iso-propylcyclopentyl, 2,6-dimethylcyclohexyl, 4-(t-butyl)cyclohexyl, 2-vinylcyclohexyl, 3-allylcyclopentyl, 3,4-diallylcyclopentyl, 1-(4-pyridinyl)piperidinyl, 1-(4-pyridinylmethyl)piperidinyl, 4-(4-pyridinyl)piperidinyl, 4-(4-pyridinyl)piperazin-1-yl, and bicyclohexyl groups.

Exemplary hydrocarbyl-substituted cycloalkenyl groups include 3-methyl-3-cyclopenten-1-yl, 3,4-dimethyl-3-cyclopenten-1-yl, 2-iso-propyl-2-cyclopenten-1-yl, 2,3-diethyl-2-cyclopenten-1-yl, 4-vinyl-1-cyclohexen-1-yl, 3,4-diethyl-3-cyclopenten-1-yl, and 3,4-diallyl-3-cyclopenten-1-yl groups.

Exemplary hydrocarbyl-substituted aryl groups include tolyl, mesityl, xylyl, cumenyl, cymenyl, 3,5-di(t-butyl)phenyl, 2-methylnaphthyl, 2-vinylphenyl, 2-vinylbenzyl, 2-vinylnaphthyl, 4-cyclohexylphenyl, biphenyl, 4-(4-piperidinyl)pyridinyl, and p-terphenyl groups.

Exemplary hydrocarbyl-substituted heteroaryl groups include 2-methylpyridin-1-yl, 2-ethylpyridin-1-yl, 3-vinylimidazol-1-yl, 2-methylimidazol-1-yl, 2-methylquinoxalin-1-yl, 1-allylbenzo-triazolyl, 2,2'-bipyridyl, 4,4'-bipyridyl, 4-methylpyrazinyl, 4-(pyridinylmethyl)-pyridinyl, 4-benzylpyrazinyl, nicotinamidyl, 2-methylfuranyl, 5-methylfurfurylamino, 2-methylthiopheneyl, 4-methyloxazolyl, 2,5-diphenyl-4-methyloxazolyl, and 4-methyl-thiazolyl groups.

The term "halogen" denotes a chloro, fluoro, bromo or iodo substituent, preferably a chloro or fluoro substituent.

The term "(interactive) binding" or "interaction" refers to any type of interactive association between a corresponding pair of molecules (e.g., ligand/target glycoprotein receptor) that exhibit mutual affinity or binding capacity. An interactive association may occur e.g. between a corresponding pair of chemically reactive groups (donor/acceptor, acid/base, etc) that exhibit mutual reactivity. Exemplary binding events include, without limitation, hydrophobic interactions, hydrophilic interactions, hydrogen bonds, van der Waals forces, ionic interactions, nonionic interactions, electrostatic interactions, covalent bonding, and the like. It is understood that depending of the nature of the binding event the interaction may be of different levels, i.e. transient or permanent, weak or strong binding.

The term "glycoprotein" (or "glycopeptides") as used herein refers to a protein (or peptide) that contains one or more covalently linked carbohydrate or oligosaccharide groups. The carbohydrate groups are typically attached through an amine side chain group, typically of the asparagine amino acid (to give N-linked carbohydrates) or through a hydroxyl side chain group, usually of the serine or threonine amino acids (to give O-linked carbohydrates) or through an indole side chain group, usually of tryptophan residues (to give C-linked carbohydrates). An oxidized glycoprotein or glycopeptide refers to a glycoprotein or glycopeptide, which has undergone treatment with a suitable oxidizing reagent thereby cleaving vicinal diol moieties of the attached carbohydrate to yield aldehyde groups. Such an oxidation of carbohydrates (to give dialdehyde carbohydrates) may be carried out according to conventional procedures e.g. using periodic acid or periodate salts, lead(IV) salts or permanganate, preferably sodium(meta)periodate. Alternatively, chemical approaches can exploit metabolic labeling of cells using analogs of glycan precursors that carry bioorthogonal groups (such as azide, alkyne, ketone or aldehyde) to generate attachment sites for the crosslinkers on glycoprotein receptors (Current opinion in chemical biology (2007) vol. 11 (1) pp. 52-8).

The terms "protein", "polypeptide", "oligopeptide" and "peptide" as used herein have the same meaning and refer to an amino acid polymer having any length (typically a peptide is referred to as a fragment of a protein). This polymer may be a straight, branched or cyclic chain. An amino acid may be a naturally-occurring or nonnaturally-occurring amino acid, or a variant amino acid. The term "fragment" with respect to a polypeptide or polynucleotide refers to a polypeptide or polynucleotide having a sequence length ranging from 1 to n–1 with respect to the full length of the reference polypeptide or polynucleotide (of length n). The length of the fragment can be appropriately changed depending on the purpose.

For the present invention a glycoprotein may be a glycoprotein that occurs in nature, or may alternatively have a sequence that was engineered synthetically (with the proviso that an engineered glycoprotein contains at least one peptide sequence that serves as a glycosylation site). A glycoprotein may be an intracellular glycoprotein, a cell surface glycoprotein (i.e. a glycoprotein bound to the surface of a cell) or a glycoprotein in solution (i.e. a glycoprotein secreted into the medium).

A glycoprotein for use in the methods of the present invention may be any pharmaceutically or commercially relevant glycoprotein with an interesting or useful biological or chemical activity, such as a receptor, antibody, enzyme, hormone, regulatory factor, antigen, binding agent etc. The following list of glycoproteins that may be used in the methods of the present invention is merely exemplary and is not intended to be a limiting recitation. A skilled person will understand that any glycoprotein may be used in the present methods and will be able to select the particular glycoprotein based on his or her particular needs.

The term "target glycoprotein receptor" or "glycoprotein receptor", also indicated by (III) herein, refers to a glycoprotein to which one or more specific kinds of ligands or signalling molecules may bind. Such a (target) glycoprotein receptor may be present in a biological fluid or on cells derived from any subject, preferably a mammalian subject, e.g. a human or animal. Thus, when used in combination with the term "cell surface" (i.e. cell-surface glycoprotein receptor) it refers to a glycoprotein being associated with the plasma membrane of a cell and having at least one amino acid exposed to the extracellular space at times, to which one or more specific kinds of ligands or signalling molecules may bind. When used in combination with the term "oxidized" it refers to a glycoprotein whose carbohydrate portions have been oxidized to form aldehyde groups by a suitable oxidative treatment or where an aldehyde group was introduced by metabolic labelling.

Glycoprotein receptors include any cell-surface receptors or any secreted receptors, such as those disclosed in Varki, A. et al.

Essentials of Glycobiology, Cold Spring Harbor Laboratory Press, 2009 and www.uniprot.org. Non-limiting examples of glycoprotein receptors include for example receptors comprising Fibroblast Growth Factor Receptor 1 (FGFR1) (Swiss-Prot Ass. Nos: Q9QZM7, Q99AW7, Q9UD50, Q63827), Fibroblast Growth Factor Receptor 2 (FGFR2) (Swiss-Prot Ass. Nos: Q96KM2, P21802, Q63241), Fibroblast Growth Factor Receptor 3 (FGFR3) (Swiss-Prot Ass. Nos: Q95M13, AF487554, Q99052), Fibroblast Growth Factor Receptor 4 (FGFR4) (Swiss-Prot Ass. No: Q91742), Neurotrophin Tyrosin Kinase Type-2 (NTRKT-2) (Swiss-Prot Ass. No: Q8WXJ5), Leukocyte Antigen Related Protein-Tyrosine Phosphatase (LAR-PT-PRF) (Swiss-Prot Ass. Nos: Q9EQ17, Q64605, Q64604, Q9QW67, Q9VIS8 P10586), Nephrin (Swiss-Prot Ass. Nos: Q925S5, Q9JIX2, Q9ET59, Q9R044, Q9QZS7, Q06500), Protein-Tyrosine Phosphatase Receptor type S (PTPRS) (Swiss-Prot Ass. Nos: Q64699, Q13332, O75870), Protein-Tyrosine Phosphatase Receptor type kappa (R-PTP-kappa) (Swiss-Prot Ass. No: Q15262), Protein-Tyrosine Phosphatase Receptor type D (PTPRD) (Swiss-Prot Ass. Nos: QBWX65, Q9IAJ1, P23468, Q64487), Ephrin type-A receptor 8 (EPHA8/Tyrosine-Protein Kinase Receptor EEK) (Swiss-Prot Ass. Nos: 009127, P29322), Ephrin type-A receptor 3 (EPHA8/Tyrosine-Protein Kinase Receptor ETK-1/GEK4) (Swiss-Prot Ass. No: P29318), Ephrin type-A receptor 2 (Swiss-Prot Ass. No: Q8N3Z2), Insulin Receptor (IR) (Swiss-Prot Ass. No: Q9PWN6), Insulin-like Growth Factor-1 Receptor (IGF-1) (Swiss-Prot Ass. Nos: Q9QVW4, P08069, P24062, Q60751, P15127, P15208), Insulin-related Receptor (IRR) (Swiss-Prot Ass. No: P14616), Tyrosine-Protein Kinase Receptor Tie-1 (Swiss-Prot Ass. Nos: 06805, P35590, Q06806), Roundabout receptor-1 (robo-1) (Swiss-Prot Ass. Nos: O44924, AF041082, Q9Y6N7), Neuronal nicotinic acetylcholine receptor alpha 3 subunit (CHRNA3) (Swiss-Prot Ass. Nos: Q8VHH6, P04757, Q8R4G9, P32297), Neuronal acetylcholine receptor alpha 6 subunit (Swiss-Prot Ass. Nos: Q15825, Q9ROW9) Platelet-Derived Growth Factor Receptor Beta (PDGFRB) (Swiss-Prot Ass. Nos: Q8R406, Q05030), Interleukin-6 Receptor (IL-6R) (Swiss-Prot Ass. No: Q00560), Interleukin-23 Receptor (IL-23R) (Swiss-Prot Ass. No: AF461422), Beta-common cytokine receptor of IL-3, IL5 and GmCsf (Swiss-Prot Ass. No: P32927), Cytokine Receptor-Like molecule 3 (CRLF1) (Swiss-Prot Ass. No: Q9JM58), Class I Cytokine Receptor (ZCYTOR5) (Swiss-Prot Ass. No: Q9UHH5), Netrin-1 receptor DCC (Swiss-Prot Ass. No: P43146), Leukocyte Fc Receptor-like Protein (IFGP2) (Swiss-Prot Ass. Nos: Q96PJ6, Q96KM2), Macrophage Scavenger Receptor 2 (MSR2) (Swiss-Prot Ass. No: Q91YK7), or Granulocyte Colony Stimulating Factor Receptor (G-CSF—R) (Swiss-Prot Ass. No: Q99062), or fragments, or variants thereof.

In other embodiments the glycoprotein receptor is selected from the group of proteoglycans. More preferably the proteoglycan is selected from the group comprising heparan sulphate proteoglycans. In the most preferred embodiment the proteoglycan is perlecan (Swiss-Prot Ass. No: P98160), or a fragment, or a variant thereof.

In yet other embodiments the glycoprotein receptor is a receptor selected from the group of membrane-anchored cell-surface enzymes. For example the cell-surface receptor is selected from the group comprising the pitrilysin family of metalloproteinases or the family of desintegrin and metalloproteases (ADAMS) comprising ADAM-8 (Swiss-Prot Ass. No: O05910), ADAM-19 (Swiss-Prot Ass. Nos: Q9H013, O35674), ADAM-8 (Swiss-Prot Ass. No: P78325), ADAM-12 (Swiss-Prot Ass. Nos: O43184, Q61824), ADAM-28 (Swiss-Prot Ass. Nos: Q9JLN6, Q61824, Q9XSL6, Q9UKQ2), ADAM-33 precursor (Swiss-Prot Ass.

Nos: Q8R533, Q923W9), ADAM-9 (Swiss-Prot Ass. Nos: Q13433, Q61072), ADAM-7 (Swiss-Prot Ass. Nos: Q9H2U9, O35227, Q63180), ADAM-1A Fertilin alpha (Swiss-Prot Ass. No: Q8R533), ADAM-15 (Swiss-Prot Ass. Nos: Q9QYV0, O088839, Q13444), Metalloproteinase-desintegrin domain containing protein (TECAM) (Swiss-Prot Ass. No: AF163291), Metalloproteinase 1 (Swiss-Prot Ass. Nos: O95204, Q9BSI6), or fragments, or variants thereof.

In some embodiments, the glycoprotein receptor may be an enzyme, such as, for example, hydrolases, transferases, isomerases, lyases, ligases, transferases and oxidoreductases. Examples of hydrolases include lipase, cholinesterase, alkaline phosphatase, β-amylase deoxyribonuclease, glucoamylase A and B, α-galactosidase I and II, β-fructofuranosidase, β-glucouronidase, N-acetyl-β-glucosaminidase, hyaluronidase, oxytocinase, kallikrein, bromelain, enterokinase, proteinase a, b, and c, pepsinogen and pepsin. Examples of oxidoreductases include glucose oxidase, peroxidase and chloroperoxidase. Examples of transferases include γ-glutamyltranspeptidase and ribonuclease. A skilled person will be aware of other known examples of enzymes that can be used in accordance with the methods of the present invention.

In further embodiments a glycoprotein receptor may be a growth factor or other signalling molecule. Growth factors are typically glycoproteins that are secreted by cells and bind to and activate receptors on other cells, initiating a metabolic or developmental change in the receptor cell. Non-limiting examples of mammalian growth factors and other signaling molecules include cytokines; epidermal growth factor (EGF); platelet-derived growth factor (PDGF); fibroblast growth factors (FGFs) such as FGF-5; insulin-like growth factor-T and -II (IGF-I and IGF-II); des(1-3)-IGF-I (brain IGF-I), insulin-like growth factor binding proteins; CD proteins such as CD-3, CD-4, CD-8, and CD-I 9; erythropoietin; osteoinductive factors; immunotoxins; bone morphogenetic proteins (BMPs); interferons such as interferon-alpha, -beta, and -gamma; colony stimulating factors (CSFs), e.g., M-CSF, GM-CSF, and G-CSF; most interleukins; tumor necrosis factor (TNF) beta; follicle stimulating hormone; calcitonin; luteinizing hormone; anticlotting factors such as Protein C; atrial natriuretic factor; lung surfactant; plasminogen activators, such as urokinase or human urine or tissue-type plasminogen activator (t-PA); hematopoietic growth factor; and enkephalinase. One of ordinary skill in the art will be aware of other growth factors or signaling molecules that can be used in accordance with the methods of the present invention.

In other embodiments a glycoprotein receptor may be a plasma membrane transporter. Plasma membrane transporters are typically glycoproteins that mediate the transport of solutes through the lipid bilayer of the plasma membrane, such as for example channels, the solute carrier superfamily, active transporters, auxiliary transport proteins or other transporters. Examples of channels include sodium channel subunit beta-1 (Swiss-Prot Ass. No: Q07699). Examples of the solute carrier superfamily include the solute carrier family 2, facilitated glucose transporter member 1 (Swiss-Prot Ass. No: P11166), the solute carrier family 22 member 1 (Swiss-Prot Ass. No: O15245) and solute carrier family 22 member 6 (Swiss-Prot Ass. No: Q4U2R8). Examples of active transporters include Sodium/potassium-transporting ATPase subunit alpha-2 (Swiss-Prot Ass. No: P50993). A skilled person will be aware of other known examples of plasma membrane transporters that can be used in accordance with the methods of the present invention The term "ligand" specific for a particular target glycoprotein receptor, also indicated by (II) herein, is used broadly in the context of the present invention. Specifically, the term refers to any compound which is able to interact or bind with a target glycoprotein receptor which is membrane-bound and located on a cell surface or in a secreted form. Each target glycoprotein receptor may have one or more specific ligand binding sites, which can be the same or different or overlapping for different ligands, and which are specific peptide domains within the whole target glycoprotein receptor (i.e. a specific portion of the protein) where ligand binding occurs. Recognition between ligand and peptide domain may be due to sequence specificity, three-dimensional structure, or post-translational modifications of the ligand or the target glycoprotein receptor. Examples of a ligand include, without limitation, a peptide, including a glycopeptide, a polypeptide, protein, including a glycoprotein or phosphoprotein, a carbohydrate, glycolipid, phospholipid, oligonucleotide, polynucleotide, aptamers, vitamin, antigens and fragments thereof, haptens, receptor agonists, partial agonists, mixed agonists, antagonists, drugs, chemokines, hormones (e.g. LH, FSH, TRH, TSH, ACTH, CRH, PRH, MRH, MSH, glucagon and prolactin; transferrin; lactoferrin; angiotensin; histamine; insulin; lectins), transmitters, autocoids; growth factors (for example PDGF, VEGF, EGF, TGFa, TBFβ, GM-CSF, G-CSF, M-CSF, FGF, IGF, bombesins, thrombopoietin, erythropoietin, oncostatin and endothelin 1), cytokines including interleukins (e.g. interleukins 1 to 15), lymphokines and cell signal molecules, such as tumor necrosis factor (e.g. tumor necrosis factors α and β) and interferons (e.g. interferons α, β and γ), prosthetic groups, coenzymes, cofactors, regulatory factors, or any other naturally occurring or synthetic organic molecule which can specifically bind to a receptor, including fragments, analogs and other derivatives thereof that retain the same binding properties. A ligand specific for a particular cell surface target glycoprotein receptor may be targeting a wide range of cell types or a specific cell type.

In some embodiments a ligand is selected from the group comprising peptides, carbohydrates, lipids or nucleotides. The term nucleotide includes natural nucleotides, nucleotide analogues, nucleotide derivatives, di-, oligo- or polynucleotides, or nucleotide comprising substances. A nucleotide analogue is defined as a molecule comprising a nucleotide base or a modified nucleotide base, a sugar residue or a modified sugar residue and a mono-, di-, tri-, quadra-, or penta-ester group. If a fragment of for example a protein is used, i.e. a peptide, it may be of any suitable length. It is understood, that the (minimal) length and composition of the peptide, i.e. the number and type of amino acids, is dictated by the nature of the binding interaction. A peptide may typically comprise for example from 3-100 amino acid residues.

In some embodiments, the ligand may be an antibody. Antibodies are heavy (~150 kDa) globular plasma proteins with oligosaccharide chains added to some of their amino acid residues. They have the ability to specifically bind a particular antigen. Given the large number of antibodies currently in use or under investigation as pharmaceutical or other commercial agents, analysis of the binding interactions with a particular ligand in accordance with the methods of the present invention is of particular interest. In some embodiments, an antibody may be a monoclonal antibody such as the therapeutic antibodies Trastuzumab and Bevacizumab. In some embodiments, a monoclonal antibody is a humanized antibody. In other embodiments, an antibody can be polyclonal.

In some embodiments, engineered affinity binders can be employed such as ankyrin repeat binders, affinity binders generated by phage display, or oligonucleic acid or peptide aptamers.

In some embodiments, the ligand may be a glycoprotein such as the glycoprotein receptors mentioned hereinabove. In some embodiments, the ligand may be a domain of a cell-surface protein such as the cell-surface glycoprotein receptors mentioned hereinabove.

In some embodiments, the ligand can be a microorganism or a virus.

According to the invention a ligand interacts with its target glycoprotein receptor through its binding site, which is a specific peptide fragment of a target glycoprotein receptor, such as a particular amino acid sequence or the three-dimensional structure of that fragment of a target glycoprotein receptor which is referred to as the binding site. The term "interact" or "interaction" with reference to a ligand binding to its (cell-surface or secreted) target glycoprotein receptor binding site includes a transient or permanent direct or indirect contact between the (cell-surface or secreted) target glycoprotein receptor and the ligand and may be characterized by its binding affinity, i.e. its dissociation equilibrium constant $K_d$. Typical binding affinities of a ligand for its target glycoprotein receptor may be at least $10^{-5}$ M, preferably $10^{-7}$ M and greater, e.g. around $10^{-8}$ M to around $10^{-12}$ M. The methods of the present invention allow the detection of both typical binding affinities as well as lower affinity interactions between a (cell-surface or secreted) target glycoprotein receptor and a ligand characterized by $K_d$ having e.g. a value of less than $10^{-5}$ M.

Thus in a first aspect, the present invention is directed towards a tri-functional crosslinking reagent. These reagents are represented by formula (I)

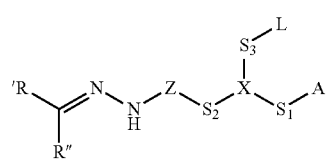

(I)

wherein
X represents a core structure;
$S_1$, $S_2$, $S_3$ represents independently of each other a spacer group;
L represents a ligand-reactive group;
A represents an affinity group;
Z represents aryl or heteroaryl;
R' represents H or an alkyl group and R" represents an alkyl group or R', R" together represent an alkandiyl to form a cyclalkyl group.

These tri-functional crosslinkers of formula (I) show beneficial effects and are particularly suited in straightforward quantitative mass spectrometric workflows for the unbiased detection of ligand interactions with target glycoprotein receptors, including plasma membrane glycoproteins on live cells (particularly in their natural interaction microenvironment without genetic manipulation) or secreted glycoproteins. These tri-functional crosslinkers may also find applications in analyzing biological fluids.

The first aspect of this the invention, compounds of formula (I), shall be explained in further detail below.

Core structure X: As apparent from the above, the inventive compounds (I) have a core structure X carrying three branches, wherein each branch comprises a different functionality (and thus the crosslinking reagent may also be termed heterotri-functional). A first branch comprises a hydrazone group (R"R'C=N—NH—) that is able to react with oxidized glycoproteins. A second branch comprises a ligand-reactive group that may be conjugated to a ligand of choice. A third branch comprises an affinity group for purification purposes, preferably affinity purification purposes of the proteins captured by the first and second functionality. These reagents are of special interest as the combination of these three different functionalities in one molecule is unique and finds use in various biomedical applications such as the detection and characterization of interactions between a ligand (II) and a target glycoprotein receptor (III). The core structure X may be any structure which allows to build on the three branches composed of spacer groups $S_1$, $S_2$, $S_3$ and the functionalities affinity group, L, and the hydrazone group. Thus, the core structure preferably carries three reactive functional groups as defined herein. Typically, the core structure and spacer groups are designed such that there is negligible or no steric hindrance between the three branches (and thus between the three functionalities -L, -affinity group and the hydrazone group).

In one embodiment, the core structure X may be a substituted hydrocarbon, such as a substituted alkyl group, for example a tri- or tetra-substituted carbon atom, e.g, the α-carbon of an α-amino acid $H_2N$—$CHR_{AA}$—COOH (with $R_{AA}$ being the amino acid sidechain). Thus, X may be a natural or unnatural amino acid having a side chain $R_{AA}$ with a reactive group. Examples of natural amino acids include e.g., lysine, serine, aspartic acid, glutamic acid, cysteine, etc. Examples of unnatural amino acids include e.g. the corresponding D-amino acids, homoserine and the like). In these embodiments, the three spacer groups $S_1$, $S_2$, $S_3$ may be linked to the amino-group and the carboxy-group and the reactive side chain group $R_{AA}$. In an advantageous embodiment, X may be a group of formula (I-I)

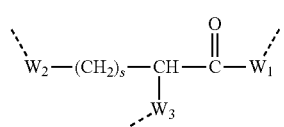

(I-I)

wherein the dotted lines represent the linkage of $W_1$, $W_2$, $W_3$ to groups $S_1$, $S_2$, $S_3$,
$W_1$ represents —NH—, —O—, —S—;
$W_2$ represents —COO—, —OOC—, —CONH—, —NHCO—, —NH—, —O—, —S—;
$W_3$ represents —COO—, —OOC—, —CONH—, —NHCO—, —NH—, —O—, —S—;
s represents an integer from 1 to 12.

It is understood that any of the three functional groups in the group of formula IV can be coupled to any of the three linkers $S_1$, $S_2$, $S_3$. In an advantageous embodiment, $W_1$ is linked to $S_1$, $W_2$ is linked to $S_2$, and $W_3$ is linked to $S_3$.

Advantageously, $W_1$ represents —NH—.
Advantageously, $W_2$ represents —CONH—.
Advantageously, $W_3$ represents —NHCO—.
Advantageously, s represents 4.

In a further embodiment, the core structure X may be a substituted aryl or heteroaryl group, which is at least trisubstituted, preferably a tri-functional 6-membered aryl or heteroaryl group of formula (I-II)

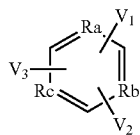
(I-II)

wherein $V_1$, $V_2$, $V_3$ are independently of each other a functional group such as carboxy, amine, hydroxyl, thiol and $R_a$, $R_b$, $R_c$ are independently of each other O or N.

In yet a further embodiment, the core structure X may be derived from a linear or cyclic glycerol or sugar moiety. A variety of sugars are available having selective (and specifically removable) protecting groups, which can be used in preparation of the tri-functional crosslinking reagents described herein.

A skilled person will know that a variety of other core structures X may provide the required scaffolding for the spacer groups and functionalities.

Functionality L: This functionality of the tri-functional crosslinking reagent (I) is a ligand-reactive group such as a reactive functional group or an activated functional group. This group serves for coupling the spacer to a ligand of choice (II) and thus for directing the tri-functional crosslinking reagent towards specific target glycoprotein receptors (III). The reactive functional groups or the activated functional groups are able to react with their reactive counterpart groups present on the ligand.

The term "reactive functional group" as used herein refers to an unprotected, free functional group (unless stated otherwise). In specific embodiments, a reactive functional group is selected from the group consisting of —COOH, —NH$_2$, —OH, —SH, —CH═CH— and —CH═CH—COOH.

Examples of activating reagents used for activating a reactive functional group include, but are not limited to, 1-hydroxybenzotriazole (HOBt), 3-hydroxy-3,4-dihydro-1,2,3-benzotriazine-4-one (HOOBt), N-hydroxysuccinimide (NHS), dicyclohexylcarbodiimide (DCC), diisopropylcarbodiimide (DIC), 1-ethyl-3-(3-dimethylaminopropyl)-carbodiimide (EDAC), 2-(1H-7-azabenztriazol-1-yl)-1,1,3,3-tetramethyluronium hexafluoro phosphate (HATU), 2-(1H-benzotriazol-1-yl)-1,1,3,3-tetramethyluronium hexafluorophosphate (HBTU), 3,4-dihydro-1,2,3-benzotriazin-4-one-3-oxy tetramethyluronium hexafluorophosphate (HDTU), benzotriazol-1-yloxytris(dimethylamino)phosphonium hexafluoro phosphate (BOP), benzotriazol-1-yloxy-tris-(pyrrolidino)-phosphonium hexafluoro phosphate (Py-Bop), (3,4-dihydro-1,2,3-benzotriazin-4-one-3-oxy)diethyl phosphate (DEPBt), 3,4-dihydro-1,2,3-benzotriazin-4-one-3-oxy tris-(pyrrolidino)-phosphonium hexafluorophosphate (PDOP), 2-(benzotriazol-1-yloxy)-1,3-dimethyl-2-pyrrolidin-1-yl-1,3,2-diazaphosph-olidinium hexafluorophosphonate (BOMP), 5-(1H-7-azabenztriazol-1-yloxy)-3,4-dihydro-1-methyl 2H-pyrrolium hexachloroantimonate (AOMP), (1H-7-azabenztriazol-1-yloxy)tris(dimethylamino) phosphonium hexafluoroposphate (AOP), 5-(1H-Benzotriazol-1-yl)-3,4-dihydro-1-methyl 2H-pyrrolium hexachloroantimonate: N-oxide (BDMP), 2-bromo-3-ethyl-4-methyl thiazolium tetrafluoroborate (BEMT), 2-bromo-1-ethyl pyridinium tetrafluoroborate (BEP), 2-bromo-1-ethyl pyridinium hexachloroantimonate (BEPH), N-(1H-benzotriazol-1-ylmethylene)-N-methylmethanaminium hexachloroantimonate N-oxide (BOMI), N,N'-bis(2-oxo-3-oxazolidinyl) phosphinic chloride (BOP—C1), 1-(1H-benzotriazol-1-yloxy)phenylmethylene pyrrolidinium hexachloroantimonate (BPMP), 1,1,3,3-bis(tetramethylene) fluorouronium hexafluorophosphate (BTFFH), chloro(4-morphoino)methylene morpholinium hexafluorophosphate (CMMM), 2-chloro-1,3-dimethyl-1H-benzimidazolium hexafluorophosphate (CMBI), 2-fluoro-1-ethyl pyridinium tetrafluoroborate (FEP), 2-fluoro-1-ethyl pyridinium hexachloroantimonate (FEPH), 1-(1-pyrrolidinyl-1H-1,2,3-triazolo[4,5-b]pyridin-1-ylmethylene)pyrrolidinium hexafluoro-phosphate N-oxide (HAPyU), O-(1H-benzotriazol-1-yl)-N,N,N',N'-bis-(pentamethylene)uronium hexafluorophosphate (HBPipU), O-(1H-benzotriazol-1-yl)-N,N,N0,N0-bis(tetramethylene)urinium hexafluorophosphate (HBPyU), (1H-7-azabenztriazol-1-yloxy) tris (pyrrolidino) phosphonium hexafluorophosphate (PyAOP), bromo-tripyrrolidinophosphonium hexafluorophosphate (PyBrOp), chloro-tripyrrolidinophosphonium hexafluorophosphate (PyClOP), 1,1,3,3-bis(tetramethylene) chlorouronium hexafluorophosphate (PyClU), tetramethylfluoro-mamidinium hexafluorophosphate (TFFH), triphosgene, triazine-based reagents [cyanuric chloride, cyanuric fluoride, 4-(4,6-dimethoxy-1,3,5-triazin-2-yl)-4-methylmorpholinium chloride (DMT-MM), 2-chloro-4,6-dimethoxy-1,3,5-triazine (CDMT)], bis(2-chlorophenyl) phosphorochloridate, diphenyl phosphorochloridate, diphenyl phosphoroazide (DPPA) and any combination thereof.

The term "activated functional group" as used herein refers to a reactive functional group that has been activated by standard chemical techniques using a coupling agent to obtain the corresponding activated functional group.

The activated functional groups can be divided into subgroups according to their specific reactivity. Thus in specific embodiments, an activated functional group is selected from the group consisting of an amine-reactive groups, a hydroxyl-reactive groups, a thiol-reactive groups, an aldehydo- or keto-reactive groups, and a carboxy-reactive group.

An "amine-reactive group" is an activated functional group reacting with (primary or secondary) amines. Typical amine-reactive groups include aryl or alkyl activated carboxylic acid esters —COOR, such as N-hydroxysuccinimide esters or derivatives thereof (e.g. sulfo-N-hydroxysuccinimide esters), phenolic esters or derivatives thereof (e.g. wherein R is phenol, p-nitrophenol, tetrafluorophenol). Other amine reactive groups include acyl chlorides (—COCl), aryl and alkyl imidates —C(NH)OMe) and alkyl or aryl isocyanates (—NCO) or isothiocyanates (—NCS).

A "hydroxyl-reactive group" is an activated functional group reacting with hydroxyls. Typical hydroxyl-reactive groups include e.g. alkyl or aryl isocyanates —NCO, and aryl or alkyl activated carboxylic acid esters —COOR.

A "thiol-reactive group" is an activated functional group reacting with thiols. Typical thiol-reactive groups include e.g. maleimides or alpha-haloamides (—NH—CO—CH$_2$—Hal).

An "aldehydo- or keto-reactive group" is an activated functional group reacting with (primary or secondary) aldehydes or ketones. Typical aldehyde- or keto-reactive groups include e.g. aryl or alkyl hydrazines (—NHNH$_2$), aryl or alkyl acylhydrazines (—CO—NHNH$_2$), alkyl or aryl hydroxylamines (—ONH$_2$).

A "carboxy-reactive group" is an activated functional group reacting with carboxylic groups. Typical carboxy-reactive group include e.g. halogen, alkyl- or arylsulfonate, hydroxyl, epoxy, mercapto, amino, isocyanato and carbodiimido groups.

It is understood, that many pairs of ligand-reactive group and reactive group present on the ligand are feasible, and a skilled person will know which ligand-reactive group to select to couple with the ligand of choice.

In an advantageous embodiment, L is an activated functional group, selected from the group consisting of an amine-reactive group, a hydroxyl-reactive group, a thiol-reactive group, an aldehydo- or keto-reactive group, preferably an amine-reactive group. Particularly preferably are aryl- or alkyl activated carboxylic acid esters —COOR, such as an N-hydroxysuccinimide ester of formula

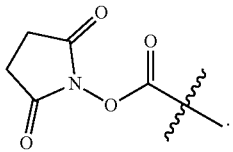 [SMILES: *C(=O)ON1C(=O)CCC1=O]

In a further advantageous embodiment, L a reactive functional group, selected from the group consisting of —COOH, —NH$_2$, —OH, —SH, —CH═CH— and —CH═CH—COOH.

Spacer Groups: As indicated hereinabove, the three spacer groups may be chosen such that steric crowding is minimized and the reactivity of the three functionalities are not compromised. Variation of linkers $S_2$ and/or $S_3$ carrying the hydrazone group and ligand-reactive group L will allow to scan the proximity of the binding site and capture different carbohydrate structures which may be located on the target receptor protein of interest itself or eventually even on neighboring molecules.

The term "spacer" as used herein, is typically a single bond or a straight-chain or branched, substituted or unsubstituted C(1-24)alkylene, wherein one or more, preferably non-adjacent, —CH$_2$— groups may independently from each other be replaced by one or more bridging groups and/or an unsubstituted or substituted cycloalkyl, heterocycloalkyl, aryl, heteroaryl; with the proviso that heteroatoms, such as O and N, are not directly linked to each other. A bridging group may replace a —CH$_2$— group within the alkylene chain or the terminal —CH$_2$— group.

A "bridging group" as used herein is selected from —CH(OH)—, —O—, —CO—, —CH$_2$(CO)—, —SO—, —CH$_2$(SO)—, —SO$_2$—, —CH$_2$(SO$_2$)—, —COO—, —OCO—, —S—CO—, —CO—S—, —SOO—, —OSO—, —SOS—, —O—CO—O—, —OCH$_2$—, —CH$_2$O—, —NR$_1$—, —NR$_1$—CO—, —CO—NR$_1$—, —NR$_1$—CO—O—, —O—CO—NR$_1$—, —NR$_1$—CO—NR$_1$—, —CH═CH—, —C≡C—, —CH═CH—COO—, —OCO—CH═CH—, —CH═N—, —C(CH$_3$)═N—, —N═N—, wherein R$_N$ represents a hydrogen atom or C(1-6)alkyl, or combinations thereof. Preferred bridging groups include —CH(OH)—, —O—, —CO—, —CH$_2$(CO)—, —COO—, —OCO—, —O—CO—O—, —OCH$_2$—, —CH$_2$O—, NR$_1$—, —NR$_1$—CO—, —CO—NR$_1$—, —NR$_1$—CO—O—, —O—CO—NR$_1$—, —NR$_1$—CO—NR$_1$—, —CH═CH—, —CH═N—, —C(CH$_3$)═N—, wherein R$_1$ represents H or C(1-6)alkyl, or combinations thereof. More preferred bridging groups include —CH(OH)—, —O—, —CO—, —CH$_2$(CO)—, —COO—, —OCO—, —O—CO—O—, —OCH$_2$—, —CH$_2$O—, NR$_1$—, —NR$_1$—CO—, —CO—NR$_1$—, wherein R$_1$ represents H or C(1-6)alkyl, or combinations thereof.

In specific embodiments, the spacer group may be a substituted or unsubstituted heteroalkylene group having 6 to 30 carbon atoms, preferably a polyethyleneglycol group (having 2 to 24 ethyleneglycol monomers in a linear configuration), a polyalcohol group, a polyamine group (e.g., spermine, spermidine and polymeric derivatives thereof), a polyester group (e.g., polyethyl acrylate) having from 3 to 15 ethyl acrylate monomers in a linear configuration), a polyamino acid group or a combination thereof.

More preferably, the spacer group may be a polyamino acid comprising 1 to 8 amino acids (i.e. an amino acid or a di-, tri-, tetra-, penta-, hexa-, hepta- or octapeptide) or a polyethyleneglycol group which is a di, tri-, tetra- penta- or hexaethylene glycol, or combinations of such polyamino acids and polyethyleneglyols. In preferred embodiments, the spacer groups $S_1$, $S_2$, $S_3$ represent independently from each other a linear chain comprising one or more repeating units of formula (a) and/or (b)

(a) —[Y$_1$—(CH$_2$)$_n$]$_p$—
(b) —[Y$_2$—(CH$_2$)$_m$—Y$_3$]$_q$—, or combinations thereof, wherein
$Y_1$, $Y_2$, $Y_3$ are independently of each other a group selected from —O—, —CO—, COO—, —OCO—, —O—CO—O—, —OCH$_2$—, —CH$_2$O—, NR$_1$—, —NR$_1$—CO—, —CO—NR$_1$—, wherein R$_1$ represents H or C(1-6)alkyl, and n, m, p, and q are independently of each other an integer from 1 to 10.

Combinations of the above group (as indicated by the wording "combinations thereof") include combinations of (a) and (b) in alternating or in block form and thus may have one of the formulas —[Y$_1$—(CH$_2$)$_n$]$_p$—[Y$_2$—(CH$_2$)$_m$—Y$_3$]$_q$—, —[Y$_2$—(CH$_2$)$_m$—Y$_3$]$_q$—[(CH$_2$)—Y$_1$]$_p$—, —[Y$_1$—(CH$_2$)$_n$]$_p$—[Y$_1$—(CH$_2$)$_m$—Y$_2$]$_q$—[(CH$_2$)$_n$—Y$_1$]$_p$— wherein $Y_1$, $Y_2$, $Y_3$ are independently of each other a group selected from —O—, —CO—, COO—, —OCO—, —O—CO—O—, —OCH$_2$—, —CH$_2$O—, NR$_1$—, —NR$_1$—CO—, —CO—NR$_1$—, wherein R$_1$ represents H or C(1-6)alkyl, n, m, p, and q are independently of each other an integer from 1 to 10.

Thus, preferred repeating units include, but are not limited to, —CO—NR$_1$—(CH$_2$)$_{n1}$—, —NR$_1$—CO—(CH$_2$)$_{n2}$—, —(CH$_2$)$_{n3}$—CO—NR$_1$—, —(CH$_2$)$_{n4}$—NR$_1$—CO—, —CO—NR$_1$—(CH$_2$)$_{n5}$—NR$_1$—CO—, —NR$_1$—CO—(CH$_2$)$_{n6}$—CO—NR$_1$—, —COO—(CH$_2$)$_{m1}$—, —OCO—(CH$_2$)$_{m2}$—, —(CH$_2$)$_{m3}$—COO—, —(CH$_2$)$_{m4}$—OCO—, —COO—(CH$_2$)$_{m5}$—OCO—, —OCO—(CH$_2$)$_{m6}$—COO—, —O—(CH$_2$)$_{p1}$—, —(CH$_2$)$_{p2}$—O—.

wherein R$_1$ represents H or C(1-6)alkyl, and n1, n2, n3, n4, n5, n6, m1, m2, m3, m4, m5, m6, p1, and p2 are independently of each other an integer from 1 to 10, preferably 1, 2, 3, 4, 5, or 6.

Other combinations of the above groups may also include combinations of various repeating units (a), for example having the following formula —[Y$_1$—(CH$_2$)$_n$]$_p$—[Y$_{1'}$—(CH$_2$)$_{n'}$]$_{q'}$—[Y$_{1''}$—(CH$_2$)$_{n''}$]$_{q''}$— wherein $Y_1$, $Y_{1'}$, $Y_{1''}$ are independently of each other a group selected from —O—, —CO—, COO—, —OCO—, —O—CO—O—, —OCH$_2$—, —CH$_2$O—, NR$_1$—, —NR$_1$—CO—, —CO—NR$_1$—, wherein R$_1$ represents H or C(1-6)alkyl, and n, n', n'' are independently of each other an integer from 1 to 10.

In an advantageous embodiment, the invention relates to compounds of formula (I) as described herein, wherein
$S_1$ represents C(1-24)alkylene;
$S_2$ represents C(1-24)alkylene;
$S_3$ represents C(1-24)alkylene;
and wherein said alkylene being a straight-chain or branched, and wherein said alkylene being substituted or unsubstituted, amd wherein one or more, preferably non-adjacent, —$CH_2$— groups of said alkylene may independently from each other be replaced by one or more bridging groups Y and/or unsubstituted or substituted cycloalkyl, unsubstituted or substituted hetero-cycloalkyl, unsubstituted or substituted aryl, unsubstituted or substituted heteroaryl; with the proviso that heteroatoms, such as O and N, are not directly linked to each other In an advantageous embodiment, the invention relates to compounds of formula (I) as described herein, wherein Y represents a group —CH(OH)—, —O—, —CO—, —$CH_2$(CO)—, —SO—, —$CH_2$(SO)—, —$SO_2$—, —$CH_2(SO_2)$—, —COO—, —OCO—, —S—CO—, —CO—S—, —SOO—, —OSO—, —SOS—, —O—CO—O—, —$OCH_2$—, —$CH_2O$—, $NR_1$—, —$NR_1$—CO—, —CO—$NR_1$—, —$NR_1$—CO—O—, —O—CO—$NR_1$—, —$NR_1$—CO—$NR_1$—, —CH=CH—, —C≡C—, —CH=CH—COO—, —OCO—CH=CH—, —CH=N—, —C($CH_3$)=N—, —N=N—; and $R_1$ represents each other hydrogen or C(1-6)alkyl independent from each other hydrogen or C(1-6)alkyl.

In a particularly advantageous embodiment, the invention relates to compounds of formula (I) as described herein, wherein Y represents —NH—CO—.

It is understood that for use in the preparation of the tri-functional crosslinkers of the invention, the spacer group is preferably provided with terminal functional groups which can be selectively protected or activated for attachment to X or one of the functionalities A, L and the aromatic hydrazine group.

Thus, in some embodiments, the spacer groups may be coupled to X and the respective functionality (A, L or the aromatic hydrazine group) through a bridging group, preferably through groups selected from —COO—, —CO—$NR_1$—, —O—, —$NR_1$—, —$NR_1$—COO—, and —S—S— linkages. It is further understood that there is no preferred order of assembling core structure, spacer and one of the three functionalities A, L and aromatic hydrazine group. A skilled person will know that depending on the nature of the various groups one order of assembly may be preferred.

Hydrazone Group: A further functionality of the tri-functional crosslinking reagent of the invention is the hydrazone group of formula

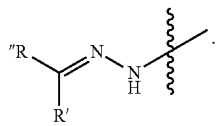

This group is capable of selectively forming a covalent bond with oxidized carbohydrate groups of glycoproteins on a cell surface or secreted glycoprotein. Said oxidized glycoproteins may be located on the cell surface or secreted glycoprotein itself or else may be located on spatially close molecules that interact with the target glycoprotein receptor. The lengths of the spacers $S_2$ and $S_3$ determine the distance between ligand binding site and said oxidized glycoproteins. Thus, varying the lengths of spacers $S_2$ and $S_3$ allows to scan or probe the immediate or expanded environment of the ligand binding site. The term "hydrazone group" includes aldehyde or ketone hydrazones having substituents selected from hydrogen, substituted (C1-C6)alkyl, substituted aryl and substituted heteroaryl. It is understood that the choice of substituent R', R" for use in the present invention may depend on the intended use of the crosslinking reagent.

In an advantageous embodiment, the invention relates to compounds of formula (I) as described herein, wherein R' represents C(1-6)-alkyl; and R" represents C(1-6)-alkyl.

In an advantageous embodiment, the invention relates to compounds of formula (I) as described herein, wherein R' and R" represent methyl.

In an advantageous embodiment, the invention relates to compounds of formula (I) as described herein, wherein Z represents an aryl group selected from unsubstituted or substituted phenyl, naphthyl, and anthracenyl.

In an advantageous embodiment, the invention relates to compounds of formula (I) as described herein, wherein Z represents a heteroaryl group selected from unsubstituted or substituted pyridyl, furyl, imidazolyl, benzimidazolyl, pyrimidinyl, thienyl, quinolinyl, indolyl, and thiazolyl; particular preferably Z is pyridyl.

Affinity Group: The term "affinity group" as used herein refers to any identifiable tag, group, or moiety that is capable of being specifically bound by another composition (optionally attached or linked to a solid support, such as a bead, a filter, a plate, a membrane, a chromatographic resin, etc.) for detection, identification and purification purposes. It is understood that many different species of affinity groups are known in the art and may be used, either individually or a combination of one or more different affinity groups for the present methods of the invention. Particularly suitable affinity groups allow for a covalent bond to a solid support. Such covalent binding facilitates isolation of oxidized glycoprotein receptors from a lysate.

A particularly preferred affinity group is the azide (—$N_3$), and thus compounds of formula (Id)

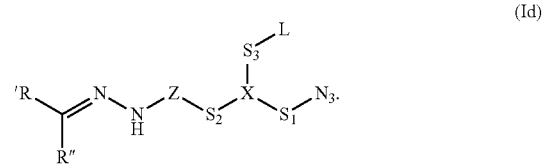

This affinity group (i.e. the azide group) is particularly useful, as it allows straightforward synthesis and purification of the compound of formula (I).

A further particularly preferred affinity group is the alkyne group —CCH, and thus compounds of formula (Ie)

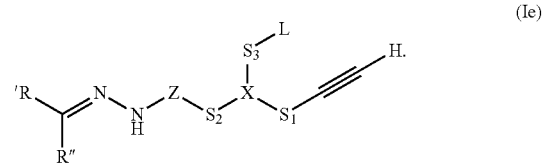

This affinity group (i.e. the alkyne group) is particularly useful, as it allows to choose from a large variety of Ligand-reactive groups L in a compound of formula (I).

In view of the above discussion, specific compounds of formula (I) were found to be particularly useful when used for characterizing and analyzing ligand-target glycoprotein interactions. The compounds are defined by formula (Ia), (Ib) and (Ic) below.

In a further embodiment, the invention relates to a compound of formula (Ia)

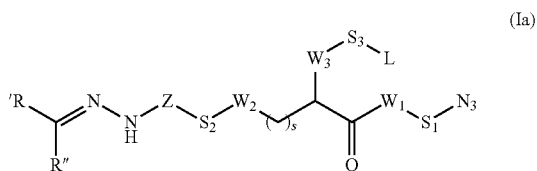

wherein
L, $S_1$, $S_2$, $S_3$, Z, R', R", s are as defined herein,
$W_1$ is —NH—, —O—, —S—,
$W_2$ is group selected from —COO—, —OOC—, —CONH—, —NHCO—, —NH—, —O—, and —S—,
$W_3$ is a group selected from —COO—, —OOC—, —CONH—, —NHCO—, —NH—, —O—, —S—.

In a further embodiment, the invention relates to a compound of formula (Ib)

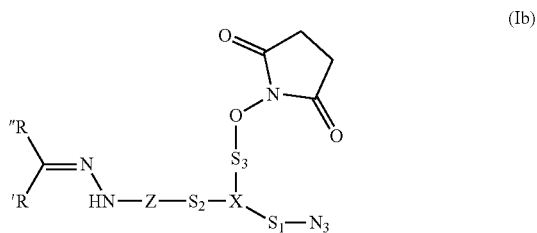

wherein the substituents are as defined in claim 1.

In a further embodiment, the invention relates to a compound of formula (Ic), this compound being known by its nickname "HATRIC",

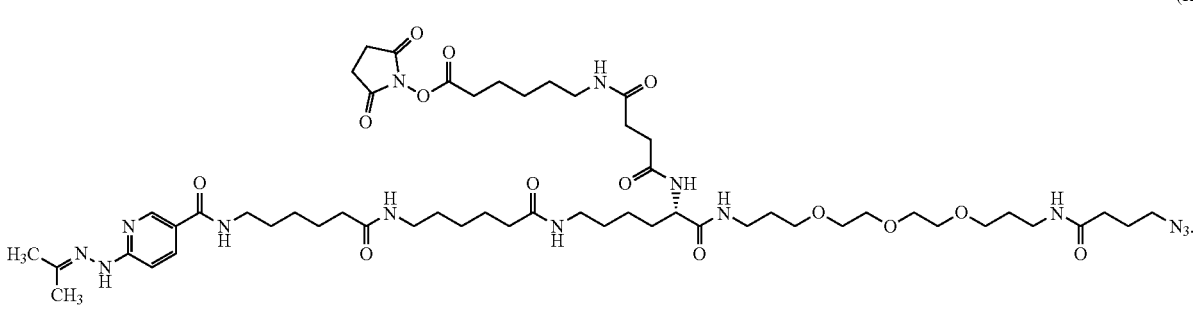

In a further advantageous embodiment, the crosslinking reagent is water soluble and/or biocompatible. The term "water soluble" typically refers to a solubility of a material in water of greater than 1 wt % based on the total weight of the material and water at 24° C. It is understood that water solubility is imparted by the hydrophilic nature of the crosslinker of the invention, more specifically by the hydrophilic nature of one or more groups of A, L, X, Z, $S_1$, $S_2$, $S_3$ and $R_N$. A skilled person will know what chemical groups to select to obtain a sufficiently hydrophilic crosslinker. In preferred embodiments, the one or more of the spacer groups $S_1$, $S_2$, and $S_3$ may comprise functional groups of more hydrophilic character to increase the hydrophilicity of the resultant crosslinking reagent. The term "biocompatible" refers to chemical inertness with respect to human cells, tissues or body fluids and minimal toxic effects of the crosslinking reagents towards such living entities.

In a second aspect, the invention is directed to the use of the tri-functional crosslinking reagents of the invention for characterizing and analyzing interactions between ligand (II) and target glycoprotein (III), see FIGS. 1 and 3.

Briefly, as shown above, the crosslinkers of the invention combine two different chemically reactive groups and an affinity group in a tri-functional molecule. The first chemically reactive group is a ligand-reactive group, preferably a N-hydroxysuccinimide, used for coupling of the crosslinker to a ligand of interest (II), which is then binding to a (cell-surface or secreted) target glycoprotein receptor of interest (III). The second chemically reactive group is an aromatic hydrazone, preferably an acetone-protected hydrazinonicotinate group, for capturing oxidized target glycoproteins. Conjugated to a ligand of interest, the affinity-tagged crosslinkers of the invention allow for the carbohydrate-directed capturing of interacting target glycoprotein receptors on oxidized live cells or in solution and the subsequent affinity enrichment of full sequence captured glycoproteins through the affinity group, preferably azide, for subsequent mass spectrometric analysis. Through the quantitative comparison with an undirected control sample, affinity tagging events (e.g. azidylation) originating from interactions of ligands with their corresponding target glycoprotein receptors can clearly be distinguished from unspecific, stochastic affinity tagging events (e.g. azidylations) of random (cell surface or secreted) proteins. This allows for the detection of even low-affinity and transient ligand-target glycoprotein receptor interactions as well as off-target effects of ligands with low-abundant glycoproteins that are present in membrane-bound form in their original cellular environment or in secreted form in a biological fluid. This is illustrated schematically in FIG. 1 in the case of cell surface target glycoprotein receptors: The ligand of interest (II) is coupled with a tri-functional crosslinker in a ligand compatible buffer solution. In a separate control reaction, an equimolar amount of crosslinker is coupled to a control protein or quenched in pure buffer solution (FIG. 1 (iii)). In order to generate aldehyde groups on cell surface carbohydrates, live cells are oxidized (FIG. 1 (ii)). The previously coupled ligands are then added to the oxidized cells to allow for the capturing of oxidized cell surface carbohydrate structure (FIG. 1 (iv a)). Thereby, random cell surface glycoproteins are labeled through stochastic events and target cell surface glycoprotein receptors for the ligand of interest are captured more efficiently through direct ligand-receptor interactions. In parallel, the control probe is added to an equal number of oxidized cells resulting in stochastic labeling events only. For all the following steps, both probes are processed in parallel. After the labeling reactions, cells are lysed (v). The remaining fractions are deterged and azide-tagged cell surface glycoproteins, are captured with an alkyne-matrix by copper-catalyzed azide-alkyne cycloaddition (FIG. 1 (vi)). Upon covalent capture of full sequence glycoproteins, these are reduced and alkylated. The covalent bond between matrix and glycoproteins allows harsh washing to remove non-covalently bound compounds. After washing, full sequence captured glycoproteins are digested with a protease, typically the serine protease trypsin, which cleaves C-terminal to arginine or lysine, but not or at low frequency before proline (FIG. 1 (vii a)). The resulting tryptic peptides differ between glycosylated peptides that are still covalently bound via HATRIC to the matrix (X) and peptides that were not glycosylated or who didn't interact with the HATRIC that are released from the matrix (IX). The released peptides (IX) are desalted and subjected to high mass accuracy mass spectrometry for identification of cell surface glycoproteins (FIG. 1 (viii)). Tryptic glycopeptides of cell surface glycoproteins remain covalently linked to the matrix (FIG. 1 (vii b)). After washing out the protease, N-glycopeptides (XI) are specifically released from the beads through an enzymatic step with PNGase F, which cleaves between the innermost component of the oligosaccharide structure and the asparagine of the glycopeptide in the N—X—S/T glycosylation motif of the peptide (wherein N stands for asparagine, X stands for any amino acid except proline, and S/T for serine or threonine, respectively). By doing so, PNGaseF deamidates the asparagine and introduces the specific N115-X-S/T signature in formerly glycosylated peptides (FIG. 1 (ix)). The released peptides are desalted and resuspended in a suitable buffer solution for the analysis with a high mass accuracy mass spectrometer. For the analysis of the two different peptide fractions (IX and XI), mass spectrometers are operated in the data dependent mode in which ion signals above a predetermined threshold automatically trigger the instrument to switch from MS to MS/MS mode for generating collision-induced dissociation (CID) or higher energy collisional dissociation (HCD) spectra of peptides. All MS/MS spectra are searched against a standard protein database. MS/MS spectra from N-glycopeptide fraction are additionally filtered for the presence of the N115-X—S/T motif. Based on both different peptide fractions (IX and XI), the concentration of cell surface peptides in the ligand sample is quantitatively compared to the control sample in order to detect specific enrichment of cell surface receptors. For stochastically tagged peptides from cell surface proteins, ratios should be around 1 and glycoprotein receptor peptides that are specifically captured in a ligand-based fashion get higher values in the ligand sample vs. control. If proteins are identified with more than one peptide, the abundance information can be combined from the two different peptide fractions.

It is contemplated that MS analysis may be replaced by other analytical methods. Such other methods being included as part of the present method.

Thus, in a third aspect, the present invention is directed towards a method of identifying specific interactions between a ligand (II) and a target glycoprotein receptor (III) in a sample by the use of a compound of formula (I). Specifically, the invention provides for such method, wherein the target (III) is a glycoprotein receptor; and wherein the ligand (II) recognizes a ligand-specific domain on the target (III); and wherein a target-ligand-reagent-complex (VI) is formed, said complex (VI) comprising a compound of formula (I) as described herein, a ligand (II) and a target (III), wherein ligand (II) is covalently bound to group L of formula (I) and target (III) is covalently bound to the hydrazone-group present in formula (I).

This aspect of the invention shall be explained in further detail below.

As indicated above, it is understood, that the target glycoprotein receptor (III) may be either in solution or on the surface of a cell (as shown in FIG. 1).

As indicated above, it is understood, that compound (I) includes a number of derivatives, as outlined in the first aspect of the invention. Thus in preferred embodiments the above method of the invention is carried out using a compound according to formula (Ia), (Ib), or (Ic).

According to this aspect, the invention is directed to a method of identifying specific interactions between a ligand (II) and a cell surface receptor having at least one aldehyde functionality (III) in a sample comprising a population of cells, wherein the ligand (II) recognizes a ligand-specific peptide domain on the target glycoprotein receptor (III). Such aldehyde functionality may be chemically induced as described herein, metabolically engineered or enzymatically produced.

In an advantageous embodiment, the inventive method comprises the steps of
i) providing a sample comprising said target (III),
ii) subjecting the target (III) to oxidative treatment to generate aldehyde functions on at least one carbohydrate residue thereby obtaining an oxidized target (IV),
iii) providing a tri-functional crosslinking reagent of formula (I) as described herein, and allowing the ligand-reactive group L thereof to conjugate to said ligand (II) to obtain a ligand-reagent-complex (V),
iv) contacting the sample of step (ii) with complex (V) of step (iii) under conditions under which (a) the complex (V) is able to bind the ligand-specific domain on the oxidized target (IV) and (b) the hydrazone group (R'R"C=N—NH—) of said complex (V) is converted to its free form and allowed to covalently bind the oxidized carbohydrate target (IV), to obtain a target-ligand-reagent complex (VI) comprising a covalently bound ligand and a covalently bound target,
v) lysing the sample of step (iv) to make membrane-embedded cell surface proteins and said complex (VI) available and reacting with matrix (VII), to obtain a matrix-bound complex (VIII)
vi) enriching said complex (VI) from the sample by using an affinity matrix (VII) to obtain a matrix-bound complex (VIII),
vii) digesting said matrix-bound complex (VIII) to obtain (a) released peptides (IX) and (b) glycopeptides bound on a matrix (X) and
viii) optionally releasing bound glycopeptides (X) from said matrix (VIII) to obtain released glycopeptides (XI)
ix) analyzing and quantifying the released peptides (IX), (XI), preferably by high mass accuracy mass spectrometry, and
x) identifying the interactions between the ligand and the target glycoprotein receptor, preferably through quantitative comparison to a control reaction.

Thus, in a typical method of the invention the steps (i) to (x) are performed. These method steps are also referred to as the "Workflow for HATRIC based LRC" and are outlined in further detail below:

Step (i): In case of cell surface glycoprotein receptors as defined herein above, the sample comprises a population of cells or tissue of which at least one expresses such a cell surface glycoprotein receptor. In case of secreted glycoproteins as defined hereinabove, the sample comprises a biological fluid comprising at least one secreted glycoprotein.

The term "sample" or "biological sample", as used herein, refers to any solid or fluid sample obtained from, excreted by or secreted by any living cell or organism, including, but not limited to, tissue culture, bioreactors, human or animal tissue, plants, fruits, vegetables, single-celled microorganisms (such as bacteria and yeasts) and multicellular organisms. For example, a biological sample can be a biological fluid obtained from, e.g., blood, plasma, serum, urine, bile, seminal fluid, cerebrospinal fluid, aqueous or vitreous humor, or any bodily secretion, a transudate, an exudate (e.g., fluid obtained from an abscess or any other site of infection or inflammation), or fluid obtained from a joint (e.g., a normal joint or a joint affected by disease such as a rheumatoid arthritis, osteoarthritis, gout or septic arthritis). A biological sample can also be, e.g., a sample obtained from any organ or tissue (including a biopsy or autopsy specimen), can comprise cells (whether primary cells or cultured cells), medium conditioned by any cell, tissue or organ, tissue culture.

The term "target" refers to glycoprotein receptor (III) and is defined above.

Step (ii): In this step, the sample is subjected to oxidative treatment to generate aldehyde groups on the carbohydrates present on the target glycoprotein receptors. This may be accomplished by using e.g. periodate (e.g. 1-2 mM $NaIO_4$). FIG. 1 outlines this step by indicating the empty diamond structure.

Step (iii): In this step, the ligand-reactive group L of the crosslinker (I), preferably an activated functional group, more preferably an N-hydroxysuccinimide group, enables the efficient coupling to ligands via primary amines under ligand compatible conditions and without loss of the hydrazone function to obtain a ligand-crosslinker complex (V).

FIG. 1 outlines this step by compound (VI) comprising the covalently bound ligand (grey circle)

In a separate control reaction, an equimolar amount of crosslinker (I) is coupled to a control protein or incubated in pure buffer solution for hydrolysis of the activated functional group, e.g. the NHS ester or the ligand-reactive group, i. e. amine-reactive, is quenched with another defined compound.

FIG. 1 outlines this step by compound (VI) comprising the covalently bound ligand (grey circle) in the left column or the quenched residue (black slash) in the right column.

Step (iv) (a): In this step, the ligand-crosslinker complex (V) is combined with a sample comprising either cell(s), tissue(s), or solution(s) comprising oxidized target glycoprotein receptor (IV) allowing the hydrazone group of the ligand-crosslinker complex to react with the oxidized carbohydrate group of (IV).

When the ligand-crosslinker complex interacts with the oxidized target glycoprotein receptor, the hydrazone group of crosslinker (I) will react with these oxidized sites and form a covalent bond (c.f. FIG. 1, 2: filled diamonds). Although the oxidation of a carbohydrate structure on a glycoprotein usually generates several potential oxidized attachment sites (as shown in FIG. 1), yet the glycoproteins captured by the hydrazone group of the ligand-crosslinking reagent-complex remain the same.

Random glycoproteins are captured through stochastic events. Without being bound to theory, it is believed that aldehyde groups in proximity to the ligand-binding site on the receptors are captured more efficiently due to local enrichment caused by the direct ligand-target glycoprotein receptor interactions. This dual labeling event per tri-functional crosslinking reagent results in a dual bound target-ligand-reagent complex (VI). Formation of this complex is key to the whole method described herein.

In analogy, a control probe (such as the quenched crosslinker, or the crosslinker conjugated with an unspecific molecule, or the crosslinker conjugated with a ligand molecule with a distinct receptor specificity) is added to an equal number of cells resulting in stochastic labeling events only. Advantageously, for all the following steps, the control probe may be processed in parallel.

Typical reaction conditions include pH 6.5-7.4, such as 6.5; temperature is 0-10° C. such as 4° C.; 10-240 min, such as 90 min. Under such conditions, the protected hydrazone group (R'R"C=N—NH—) is converted to its free form and allowed to covalently bind the oxidized carbohydrate of the glycoprotein target receptors (and other glycoprotein receptors).

Step (iv) (b): In this step, which is optional, a catalyst (XX) is added to the combination of the ligand-crosslinker complex (V) with a sample comprising either cell(s), tissue(s), or solution(s) comprising oxidized target glycoprotein receptor (IV). This allows the hydrazone group of the ligand-crosslinker complex to react with the oxidized carbohydrate group of (IV) at physiological pH.

Suitable catalysts (XX) are identified below.

Advantageously, an apt buffer from the group of buffers allowing a physiological reaction between the ligand and the glycoprotein target receptor, i. e. phosphate-buffered saline, is provided. Advantageously, the amount of catalyst is in the range of 5 mM. Advantageously, the pH is from 6.5 to 7.4, which resembles the physiological conditions.

Performing the inventive method under physiological pH is considered a major advantage. Details on the catalyst (XX) are provided below, 4th aspect.

Step (v): In this step, the dual-bound target-ligand-reagent complex (VI) and random glycoprotein-reagent complexes (VIR) are released from the sample by lysis of cells and membranes, accordingly. Lysis of the sample of step (iv) makes membrane-embedded cell surface proteins and said complex (VI) available and reacts with matrix (VII), to obtain a matrix-bound complex (VIII).

In case of a method of identifying specific interactions between a ligand and a target glycoprotein receptor, wherein the target glycoprotein receptor is a cell surface glycoprotein such as a cell surface receptor, the sample comprising the cells is first subjected to a lysis step to obtain a processed cell sample comprising the dual protein-bound complex.

The dual-bound target-ligand-reagent complex is then affinity purified using its third functionality, which is the affinity group. If e.g. azide is used as the affinity group, the dual-bound target-ligand-reagent complex is affinity purified using alkyne beads in a copper-catalyzed cycloaddition reaction with an alkyne-containing matrix, i. e. alkyne agarose or alkyne magnetic beads. This results in a triple-bound target-ligand-reagent complex covalently bound to the matrix. Suitable are, for example alkyne agarose beads in a copper-catalyzed cycloaddition reaction. Typical reaction conditions are known and include 1 mM $CuSO_4$, 6.25 mM THPTA and 2 mM sodium ascorbate for 6-24 hrs, e.g. 18 hrs, at 10-30° C., e.g. room temperature.

Step (vi): In this step, the target-ligand-reagent complex (VI) is covalently bound to the affinity matrix and purified from the sample.

Other proteins from the lysed sample, mainly from intracellular space are washed away using protein-compatible buffers. Suitable buffers do not modify primary amino acid sequence of the glycoprotein. Such buffers are known and include a combination of 1% sodium dodecyl sulfate, 8M urea, 20% acetonitrile, 5M sodium chloride, 80% isopropanol, 100 mM sodium bicarbonate, pH 11.

Step (vii)a: In this step, the sample is processed and subjected to an enzymatic or chemical digestion that releases peptides of glycosylated proteins that are not covalently bound to matrix by a tagged glycoprotein.

In an embodiment of the method, proteases are use e.g., by exposure to an agent such as trypsin, chymotrypsin, Endoproteinase AspN, Endoproteinase Lys C etc. of a combination thereof, preferably using trypsin. Trypsin cleaves proteins C-terminally to arginine or lysine, but not or at low frequency before proline.

Step (vii)b: In this step, N-glycopeptides that remain covalently bound to the matrix in step (vi)a are washed to remove residual protease from step (vii) a.

If the protease of step (vii)a is not removed accordingly, following digestion steps with endo- and exoglycosidases can be hampered by proteolysis of the latter.

Step (viii): In this step, the so obtained released peptides (IX) are analyzed. Any method for analyzing such compounds available in the field may be used, a preferred method is mass spectrometry. Methods of mass spectrometry analysis are well known to those skilled in the art (see, for example, Yates, J. Mass Spect. 33:1-19 (1998); Kinter and Sherman, Protein Sequencing and Identification Using Tandem Mass Spectrometry, John Wiley and Sons, New York (2000); Aebersold and Goodlett, Chem. Rev. 101:269-295 (2001)). For high resolution polypeptide fragment separation, liquid chromatography ESI-MS/MS or automated LC-MS/MS, which utilizes capillary reverse phase chromatography as the separation method, can be used (Yates et al., Methods Mol. Biol. 112:553-569 (1999)). Preferably, data dependent collision-induced dissociation (CID) or higher-energy collisional dissociation (HCD) with dynamic exclusion will be used as the mass spectrometric method of choice (Goodlett et al., Anal. Chem. 72:1112-1118 (2000)). For such an analysis, mass spectrometers are typically operated in the data dependent mode in which ion signals above a predetermined threshold automatically trigger the instrument to switch from MS to MS/MS mode for generating collision-induced dissociation (CID) or higher-energy collisional dissociation (HCD) spectra of peptides.

Advantageously, all MS/MS spectra are searched against a standard protein database using standard algorithms (such as SEQUEST, Mascot, X!tandem, OMSSA) and are typically filtered in order to limit the false-positive protein identification rate to below 1%.

Additionally, all inferred glycoproteins are filtered for cell surface annotation.

Advantageously, step (viii) includes the step of analyzing the released peptides obtained in step (vii) (a) by quantitative mass spectrometric methods and thereby identifying the interaction between the ligand (II) and the target (III).

Advantageously, the concentration of glycoproteins in the ligand sample can quantitatively be compared to the control sample.

This allows to detect specific enrichments of target glycoprotein receptors. For this label-free mass spectrometric quantification, the reversed phase chromatography immediately preceding the mass spectrometric analysis can be displayed as a MS feature map in which the retention time of features is plotted against their mass/charge ratio. As detected by the mass spectrometer, peptides in such a map appear in distinct isotopic patterns over a defined time and with a defined ion current intensity according to their abundance in the sample. Once the peptides have been identified through fragmentation and MS/MS analysis, this information can be assigned to specific peptide features in the MS map and combined with the semi-quantitative data with open source or commercial algorithms like Superhirn (Mueller et al. Proteomics (2007) vol. 7 (19) pp. 3470-3480), or Progenesis LC-MS (Nonlinear Dynamics). MS feature maps of different samples (e.g. sample vs control) can then be overlaid and compared in order to get ratios for the peptide abundances. For stochastically tagged peptides from glycoproteins these ratios should be around 1 and glycoprotein receptor peptides that are specifically captured in a ligand-based fashion get higher values in the ligand sample vs. control. If proteins are identified with more than one peptide, the abundance information can be combined.

In other embodiments, alternative mass spectrometry-based quantification methods can be used such as
  single reaction monitoring (SRM);
  stable isotope labeling with amino acids in cell culture
    (SILAC; see e.g.: Nilsson et al. Mass spectrometry in
    high-throughput proteomics: ready for the big time. Nat
    Methods (2010) vol. 7 (9) pp. 681-5);
  Data-independent acquisition of mass spectra (SWATH
    MS; see e. g.: Gillet et al. Targeted Data Extraction of
    the MS/MS Spectra Generated by Data-independent
    Acquisition: A New Concept for Consistent and Accurate Proteome Analysis)
  Tandem Mass Tag (TMT; see e.g.: Dayon et al. Relative
    Quantification of Proteins in Human Cerebrospinal
    Fluids by MS/MS using 6-Plex Isobaric Tags)

Step (ix): In this, N-glycopeptides that remain bound to the matrix in step (vi) b are specifically released from the beads by cleaving the carbohydrate structure.

In an embodiment of the method, glycanases are use e.g., by exposure to an agent such as PNGase F, PNGase A, etc., preferably using PNGaseF. PNGaseF treatment cleaves between the innermost component of the oligosaccharide structure and the asparagine of the glycopeptide in the N—X—S/T glycosylation motive of the peptide (wherein N stands for asparagine, X stands for any amino acid except proline, and S/T for serine or threonine, respectively), thereby effecting peptide release (and concomitantly deamidation of the asparagine).

Although exemplified herein with N-linked glycosylation sites, it is understood that methods of the invention can also be used with other types of authentically identified glycosylation sites, such as O-linked glycosylation sites or possibly with other types of posttranslational modifications (e.g. attachment of glycosylphosphatidylinositol to the C-terminus of peptides) or glycosylated organic compounds other than proteins such as glycolipids etc.

Thus step (v) of the above method preferably includes separating the captured peptides from the purified dual peptide-bound complex obtained in step (iv) by subjecting it to glycosidase treatment, preferably treatment with different endo- and exoglycosidases, to obtain released peptides. Alternatively, cleavable linkers may be used, e.g. disulfide bond or cis-diol containing linkers that can be cleaved with reducing agents or periodate, respectively.

Step (x): In this step, the so obtained released peptides (XI) are analyzed. Any method for analyzing such compounds available in the field may be used, a preferred method is mass spectrometry. Methods of mass spectrometry analysis are well known to those skilled in the art (see, for example, Yates, J. Mass Spect. 33:1-19 (1998); Kinter and Sherman, Protein Sequencing and Identification Using Tandem Mass Spectrometry, John Wiley and Sons, New York (2000); Aebersold and Goodlett, Chem. Rev. 101:269-295 (2001)). For high-resolution polypeptide fragment separation, liquid chromatography ESI-MS/MS or automated LC-MS/MS, which utilizes capillary reverse phase chromatography as the separation method, can be used (Yates et al., Methods Mol. Biol. 112:553-569 (1999)). Preferably, data dependent collision-induced dissociation (CID) or higher-energy collisional dissociation (HCD) with dynamic exclusion will be used as the mass spectrometric method of choice (Goodlett et al., Anal. Chem. 72:1112-1118 (2000)). For such an analysis, mass spectrometers are typically operated in the data dependent mode in which ion signals above a predetermined threshold automatically trigger the instrument to switch from MS to MS/MS mode for generating collision-induced dissociation (CID) or higher-energy collisional dissociation (HCD) spectra of peptides.

Advantageously, all MS/MS spectra are searched against a standard protein database using standard algorithms (e.g. SEQUEST, Mascot, X!tandem, OMSSA) and are typically filtered in order to limit the false-positive protein identification rate to below 1%. Additionally, all peptides are filtered for the N115-X—S/T motif of formerly glycosylated peptides.

Advantageously, step (x) includes the step of analyzing the released peptides obtained in step (ix) by quantitative mass spectrometric methods (such methods being discussed above for step (viii) and thereby identifying the interaction between the ligand (II) and the target (III).

Advantageously, the concentration of glycoproteins in the ligand sample can quantitatively be compared to the control sample, details being provided above, step (viii).

In other embodiments, alternative mass spectrometry-based quantification methods can be used as discussed above, step (viii).

Control Reaction: Performing a control reaction is within the knowledge of the skilled person. Such control reaction may be either a hydrolysis reaction (where no ligand is added) or a quenching reaction (where a ligand with known receptor preference is added). In principle, such reaction is performed in analogy to the workflow discussed herein, steps (i) to (x), with the following deviation, also schematically illustrated in FIGS. 1 and 3, right hand (quenched residue illustrated as black slash):

In LRC experiments, a control sample is typically produced in parallel to be able to compare glycoprotein abundance in the sample to a control. With this sample, one can estimate stochastic binding of the crosslinker (I) to random cell surface glycoproteins on a given cell line, tissue or in biological fluid. To this end, the crosslinker (I) is either incubated in pure buffer solution for hydrolysis of the activated functional group L (e. g. the NHS ester is hydrolysed) or the ligand-reactive group L (e. g. NHS ester reacts with primary amines of a ligand to yield a stable amide bond) is quenched with a ligand with known binding preferences.

If the ligand-reactive group of the crosslinker (I) is hydrolysed or quenched with a compound containing a primary amine, e. g. glycine, it is possible to estimate the background binding of crosslinker (I) by means of the relative abundance of random cell surface glycoproteins on a given cell line, tissue or in biological fluid. If the ligand-reactive group of the crosslinker (I) is coupled to a ligand with known glycoprotein target receptors, the identification of the glycoprotein target receptor can serve as a quality control of the experiment. Quenching is illustrated in FIGS. 1 and 3 right hand side in that no compound (II) is present; the quenching molecule being attached to compound (I) is indicated as a black slash.

If one compares the ratio of the amount of a given glycoprotein in the ligand to the control samples, stochastically tagged glycoproteins have a ratio around 1. Glycoprotein target receptor peptides that have a ratio higher then one are specifically captured in a ligand-dependent fashion.

Comparison between reaction and control reaction allows to identify a signal Δ, as visualized in FIGS. 1 and 3.

In a fourth aspect the invention is directed towards the use of specific organic compounds as catalysts in biochemical reactions, particularly in the methods described herein (3rd aspect). This aspect of the invention shall be explained in further detail below:

Organic Compounds in the context of this aspect of the invention comply with formula (XX)

wherein n represents 1 or 2; m represents 0, 1, or 2; $R^4$ represents $NH_2$; $R^5$ represents C(1-6)alkyl or C(1-6)alkoxy.

Advantageously, $R^4$ is in the ortho-position and n=1.

Advantageously, $R^5$ represents methoxy and m=1.

The term biochemical reactions is known and specifically relates to reactions where biomolecules, such as carbohydrate structures on cell surface proteins, are chemically converted, particularly oxidized.

In a preferred embodiment, the term biochemical reactions refers to biochemical reactions on living cells.

In a preferred embodiment, the term biochemical reactions refer to step (iv) as described in the third aspect of the invention. It was surprisingly found that by including a water-soluble organic compound of formula (XX) into step (iv) b, hydrazone formation between the hydrazone group of the tri-functional crosslinking reagent and aldehydes, generated through oxidation of carbohydrate structures on cell surface proteins, occurred at pH 7.4 until saturation.

In a fifth aspect the invention is directed to a kit comprising a tri-functional crosslinking reagent as described herein (1st aspect) and optionally an organic compound as described herein (4th aspect).

The present invention is further illustrated by the following non-limiting examples:

General

Unless otherwise noted, all reactions were carried out under an ambient atmosphere, and all reagents were purchased from commercial suppliers and used without further purification. Analytical thin layer chromatography (TLC) was performed on Merck silica gel 60 F254 TLC glass plates and visualized with 254 nm light and p-Anisaldehyde staining solution followed by heating. Purification of reaction products was carried out by flash chromatography using Brunschwig silica 32-63, 60 Å under 0.3-0.5 bar pressure, by reversed phase chromatography using Acros Organics Silica gel, C18-RP, 23% C, 40-63 μm or by size exclusion chromatography using Aldrich Sephadex LH-20.

The mono-protected diamine 7,[1] 6-(2-(tert-butoxycarbonyl) hydrazinyl)nicotinic acid[2] and γ-azidobutyric acid[3] were prepared following published procedures.

[1] H NMR spectra were recorded on a Bruker AV 600 MHz spectrometer and are reported in ppm with the solvent resonance employed as the internal standard (DMSO at 2.50 ppm). Peaks are reported as (s=singlet, d=doublet, t=triplet, q=quartet, m=multiplet or unresolved, br=broad signal, coupling constant(s) in Hz, integration). $^{13}$C NMR spectra were recorded with $^1$H-decoupling on a Bruker AV 151 MHz spectrometer and are reported in ppm with the solvent resonance employed as the internal standard (DMSO-$d_6$ at 39.52 ppm).

Infrared spectra were measured neat on a Perkin-Elmer UATR Two Spectrometer. The peaks are reported as absorption maxima (n, cm$^{-1}$)

High resolution mass spectral data were obtained on a Varian IonSpec spectrometer (ESI) and are reported as (m/z).

Optical rotations were measured with a Jasco P-2000 Polarimeter, 10 cm, 1.0 mL cell.

[1] W. Liu, F. Li, X. Chen, J. Hou, L. Yi, Y.-W. Wu *J. Am. Chem. Soc.* 2014, 136, 4468-4471.
[2] B. Teng, Y. Bai, Y. Chang, Y. Chen, Z. Li *Bioorg. & Med. Chem. Lett.* 2007, 17, 3440-3444.
T.-B—Yu, J.-Z. Bai, Z. Guan *Angew. Chem. Int. Ed.* 2009, 48, 1097-1101.

EXAMPLE 1

Synthesis of Crosslinker "HATRIC"

1. Synthesis of 6-(6-((tert-butoxycarbonyl) amino) hexanamido) hexanoic acid (3)

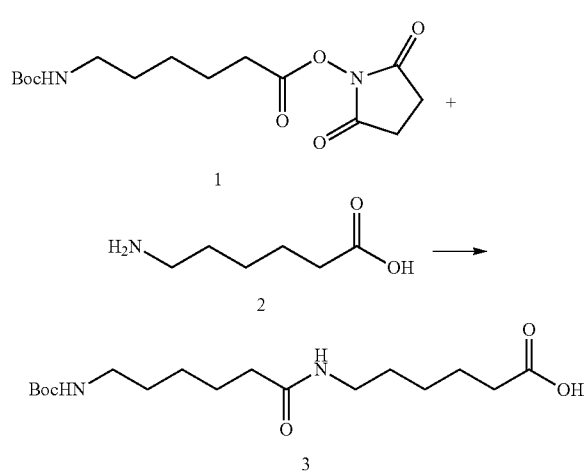

A solution of 2 (6.59 g, 50.2 mmol, 1.1 equiv) in DMF (150 mL) was treated with triethylamine (5.08 g, 50.2 mmol, 1.1 equiv) and 1 (15.0 g, 45.7 mmol, 1.0 equiv). After 3 h at room temperature, the reaction mixture was diluted with water (250 mL) and extracted with EtOAc (3×250 ml). The combined organic phases were washed with 5% aq. LiCl solution (3×250 mL), dried over MgSO$_4$, filtered and evaporated to give a white solid. The product was purified by re-crystallization from ethyl acetate/hexane (1:1, 350 ml) to give 3 (17.5 g, 90%) as white crystals.

2. Synthesis of tert-butyl 6-(((benzyloxy)carbonyl) amino) hexanoate (5)

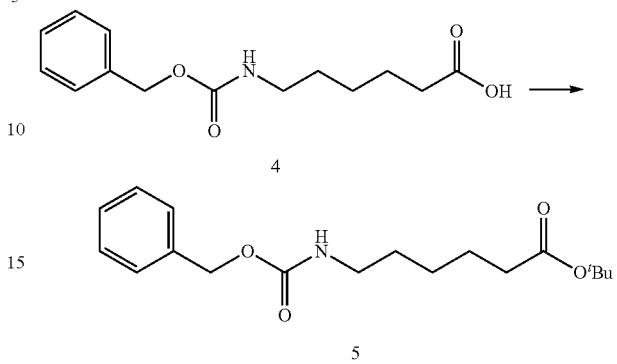

A solution of 4 (15.0 g, 56.5 mmol, 1.0 equiv) in DMF (100 mL) was treated with DMAP (2.76 g, 22.6 mmol, 0.4 equiv), tert-butanol (12.6 g, 170 mmol, 3.0 equiv), EDC.HCl (15.2 g, 79.0 mmol, 1.4 equiv) and Hünig's base (23.7 mL, 136 mmol, 2.4 equiv). After 14 h at RT, the reaction mixture was diluted with DCM (300 mL) and washed with 10% aq. citric acid solution (3×250 ml). The organic phase was dried over MgSO$_4$, filtered and concentrated under reduced pressure. The product was purified by column chromatography (200 g SiO$_2$; ethyl acetate/hexanes 5:95, then ethyl acetate/hexanes 25:75) to give 5 (14.6 g, 81%) as a colorless oil.

3. Synthesis of 4-((6-(tert-butoxy)-6-oxohexyl) amino)-4-oxobutanoic acid (6)

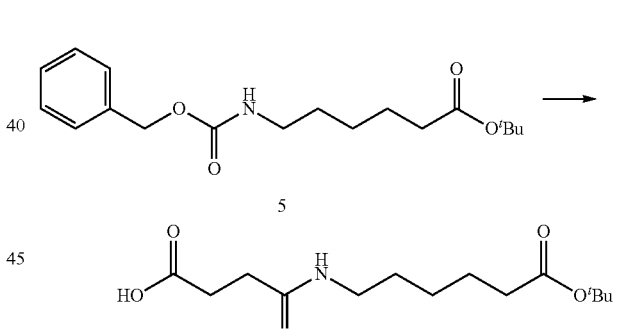

A solution of 5 (14.0 g, 43.6 mmol, 1.0 equiv) in THF/water (5:1, 100 mL) was treated with acetic acid (2.64 g, 44.0 mmol, 1.0 equiv) and 10 wt % Pd/C (1.85 g, 1.74 mmol, 4 mol %). The mixture was stirred at room temperature under an atmosphere of H$_2$ for 16 h. Then the reaction mixture was centrifuged, the supernatant was filtered through celite, concentrated under reduced pressure and the resulting oil was dried in vacuo. This oil was dissolved in DCM (150 mL) and treated with triethylamine (15.2 mL, 109 mmol, 2.5 equiv) and succinic anhydride (4.79 g, 47.9 mmol, 1.1 equiv). The reaction mixture was stirred for 3 h at room temperature, then diluted with DCM (350 mL) and washed with 10% aq. citric acid solution (3×250 mL). The product was purified by flash chromatography (150 g SiO$_2$; DCM, then DCM/MeOH 90:10) to give 6 (11.7 g, 94%) as a white solid.

4. Synthesis of allyl tert-butyl (((oxybis(ethane-2,1-diyl))bis(oxy))bis(propane-3,1-diyl))dicarbamate (8)

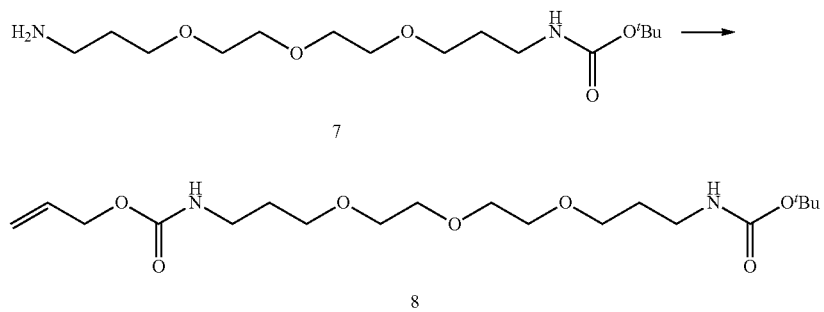

A solution of 7 (10.8 g, 30.3 mmol, 1.0 equiv) in DCM (400 mL) was treated at 4° C. with triethylamine (5.29 mL, 37.9 mmol, 1.3 equiv), followed by allyl chloroformate (3.56 mL, 33.4 mmol, 1.1 equiv). After 15 min, the reaction was allowed to warm to room temperature and was stirred for 2 h. Then, the reaction mixture was washed with water (3×250 mL), dried over MgSO$_4$, filtered and concentrated under reduced pressure. The product was purified by flash chromatography (200 g SiO$_2$; ethyl acetate/hexanes 1:1, then ethyl acetate) to give 8 (11.0 g, 90%) as a colorless oil.

5. Synthesis of (S)-(9H-fluoren-9-yl)methyl allyl tert-butyl (15-oxo-4,7,10-trioxa-14-azaicosane-1,16,20-triyl)tricarbamate (10)

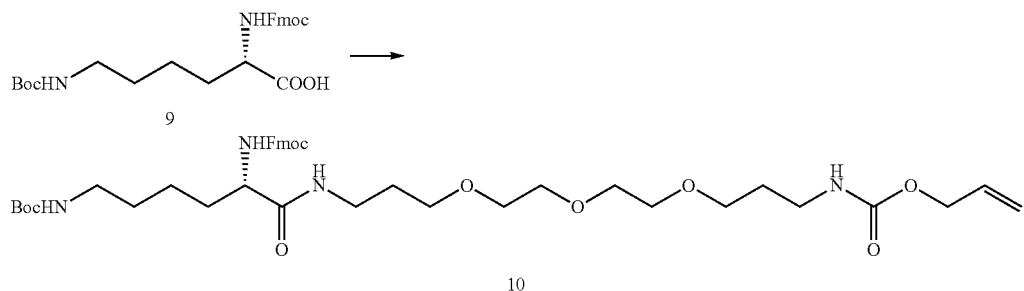

A solution of 8 (2.83 g, 7.00 mmol, 1.2 equiv) in DCM (10 mL) was treated with TFA (9 mL) and stirred for 30 min at room temperature. Then, toluene (20 mL) was added and the mixture was evaporated. Co-evaporation with toluene (3×30 mL) resulted in a brown oil, which was dried in vacuo. The residue was dissolved in DMF (20 mL), 9 (2.85 g, 6.09 mmol, 1.0 equiv) was added, followed by Hünig's base (3.40 mL, 24.4 mmol, 4.0 equiv) and HATU (2.55 g, 6.70 mmol, 1.1 equiv). The reaction mixture was stirred at room temperature for 30 min, then diluted with ethyl acetate (100 mL), washed with sat. aq. NaCl (3×100 mL), dried over Na$_2$SO$_4$, filtered and concentrated under reduced pressure. The product was purified by flash chromatography (100 g SiO$_2$; DCM, then DCM/MeOH 96:4) to give 10 (4.53 g, 99%) as a colorless oil, that solidified upon standing.

6. Synthesis of (S)-(9H-fluoren-9-yl)methyl allyl tert-butyl (15,22,29-trioxo-4,7,10-trioxa-14,21,28-triazatetratriacontane-1,16,34-triyl)tricarbamate (11)

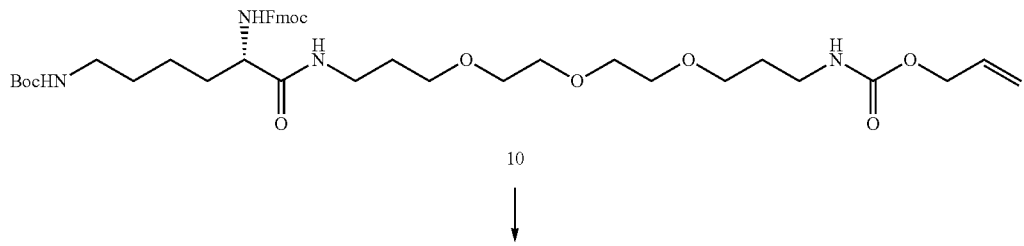

-continued

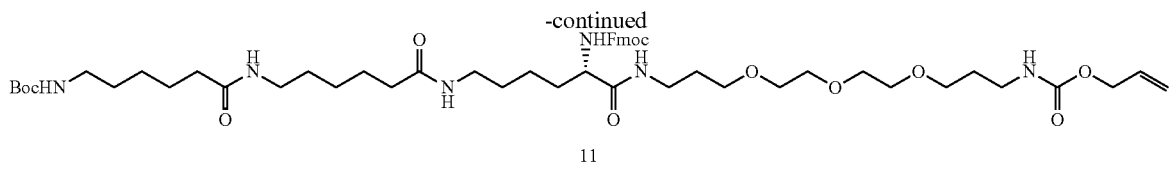

11

A solution of 10 (6.00 g, 7.95 mmol, 1.0 equiv) in DCM (25 mL) was treated with TFA (15 mL) and stirred at room temperature for h. Then, toluene (30 mL) was added and the mixture was evaporated. Co-evaporation with toluene (3×30 mL) resulted in an oil, which was dried in vacuo. The residue was dissolved in DMF (20 mL) and 3 (3.01 g, 8.74 mmol, 1.1 equiv) was added, followed by Hünig's base (6.25 mL, 35.8 mmol, 4.5 equiv) and HATU (3.32 g, 8.74 mmol, 1.1 equiv). The reaction mixture was stirred at room temperature for 30 min, then diluted with ethyl acetate (150 mL), washed with water (3×100 mL), 5% aq. LiCl (150 mL) dried over $MgSO_4$, filtered and concentrated under reduced pressure. The product was purified by flash chromatography (100 g $SiO_2$; DCM, then DCM/MeOH 90:10) to give 11 (5.90 g, 76%) as a colorless oil.

7. Synthesis of (S)-tert-butyl 2-(5-((22-((((9H-fluoren-9-yl)methoxy)carbonyl)amino)-5,21,28,35-tetraoxo-4,10,13,16-tetraoxa-6,20,27,34-tetraazatetracont-1-en-40-yl)carbamoyl)pyridin-2-yl)hydrazinecarboxylate (12)

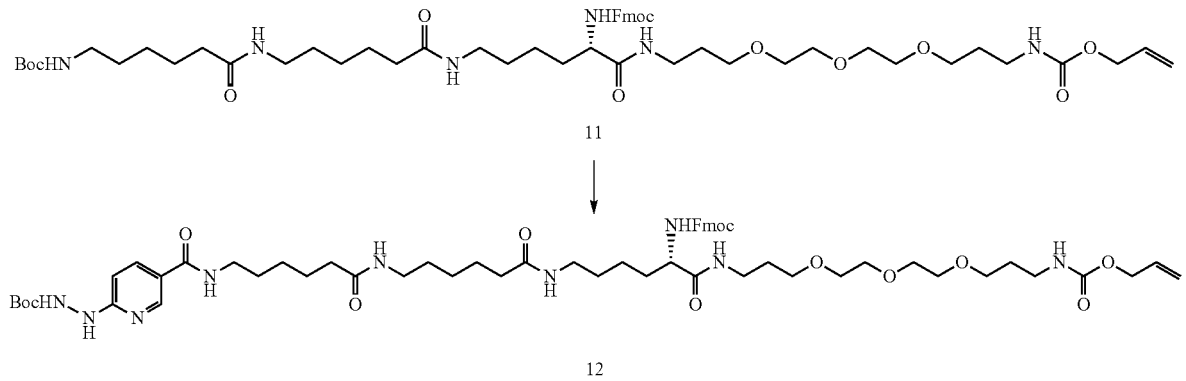

A solution of 11 (5.85 g, 5.96 mmol, 1.0 equiv) in DCM (12 mL) was treated with TFA (9 mL) and was stirred for 1 h at room temperature. Then, toluene (30 mL) was added and the mixture was evaporated. Co-evaporation with toluene (3×30 mL) resulted in an oil which was dried in vacuo. The residue was dissolved DMF (25 mL), treated with 6-(2-(tert-butoxycarbonyl) hydrazinyl)nicotinic acid (1.79 g, 7.06 mmol, 1.2 equiv), Hünig's Base (4.69 mL, 26.8 mmol, 4.5 equiv) and HATU (2.49 g, 6.56 mmol, 1.1 quiv). After 30 min at room temperature, the reaction mixture was diluted with DCM (150 mL) and washed with water (3×100 mL).

The product was purified by flash chromatography (100 g $SiO_2$; DCM, then DCM/MeOH 90:10) to give 12 (5.01 g, 75%) as a colorless foamy solid.

8. Synthesis of (S)-tert-butyl 22-(4-(6-(6-(6-(2-(tert-butoxycarbonyl)hydrazinyl)nicotinamido)hexanamido)hexanamido)butyl)-5,21,24,27-tetraoxo-4,10,13,16-tetraoxa-6,20,23,28-tetraazatetratriacont-1-en-34-oate (13)

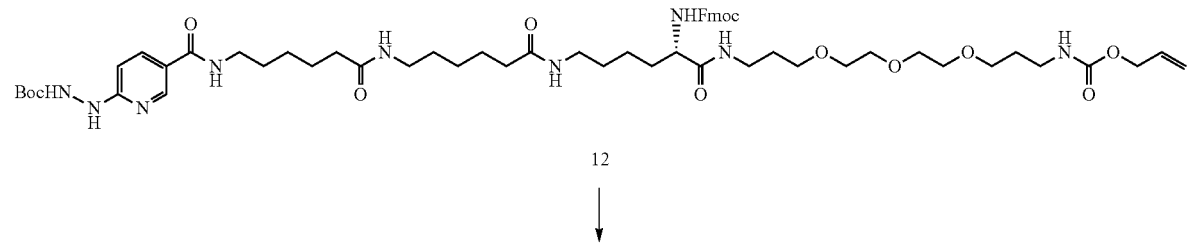

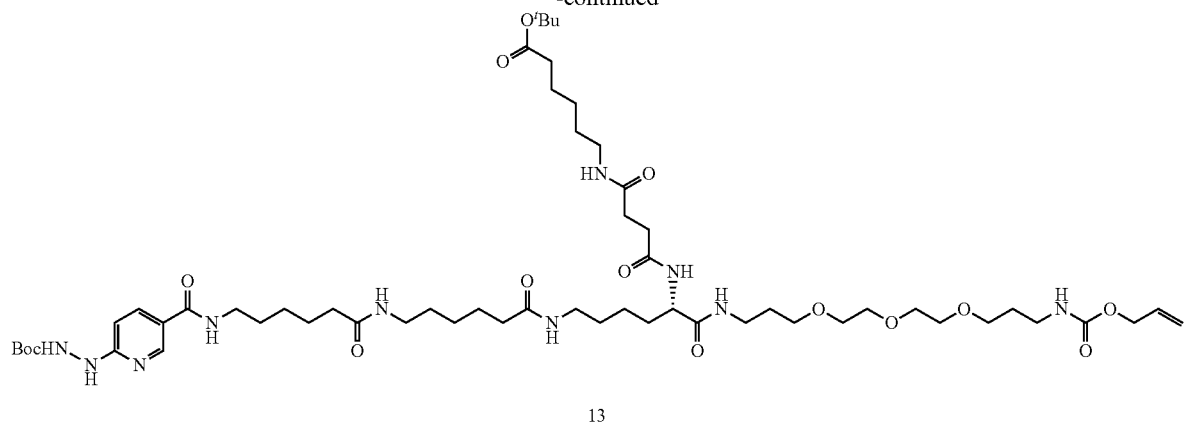

13

A solution of 12 (4.99 g, 4.47 mmol, 1.0 equiv) DMF (15 mL) was treated with piperidin (2 mL) and stirred for 1 h at room temperature. Then toluene (15 mL) was added and the mixture was evaporated. Co-evaporation with toluene (3×15 ml) resulted in an oil which was dried in vacuo. The residue was dissolved in DMF (15 mL) and treated with 6 (1.54 g, 5.36 mmol, 1.2 equiv), triethylamine (2.65 mL, 19.0 mmol, 4.3 mmol) and HATU (1.87 g, 4.92 mmol, 1.1 equiv). After 30 min at room temperature, the reaction mixture was diluted with ethyl acetate (300 mL) and washed with water (3×300 mL) and with 5% aq. LiCl (1×300 mL). The product was purified by flash chromatography (75 g SiO$_2$; DCM, then DCM/MeOH 15:1, then DCM/MeOH 9:1) to give 13 (4.69 g, 90%) as a colorless foamy solid.

9. Synthesis of (S)-tert-butyl 1-azido-21-(4-(6-(6-(6-(2-(tert-butoxycarbonyl)hydrazinyl)nicotinamido)hexanamido)hexanamido)butyl)-4,20,23,26-tetraoxo-9,12,15-trioxa-5,19,22,27-tetraazatritriacontan-33-oate (14)

13

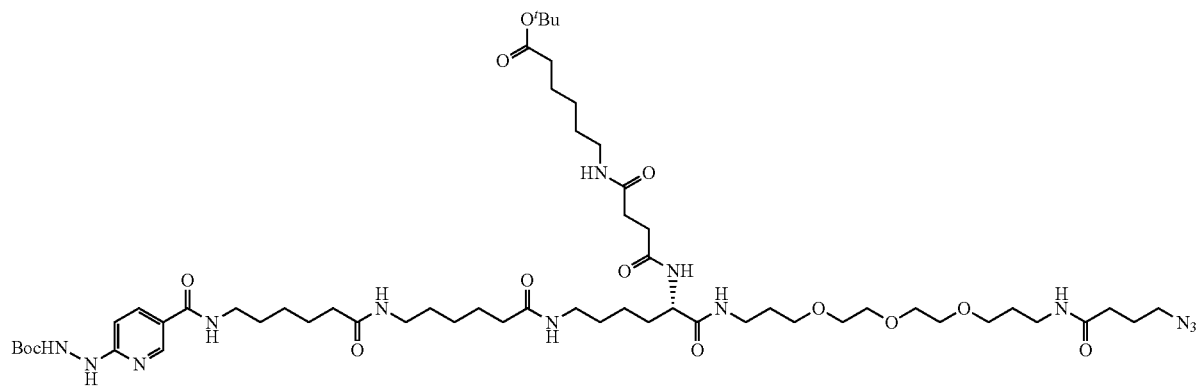

14

A solution of 13 (1.41 g, 1.17 mmol, 1.0 equiv) in MeOH (4 mL) was treated with diethylamine (0.54 mL, 5.27 mmol, 4.5 equiv), followed by a solution of Pd(PPh$_3$)$_4$ (67.6 mg, 0.0585 mmol, 5 mol %) and PPh$_3$ (33.8 mg, 0.129 mmol, 10 mol %) in DCM (8 mL). After 30 min at room temperature, the reaction mixture was evaporated. Co-evaporation with toluene (3×15 mL) resulted in an oil which was dried in vacuo. The residue was dissolved in DMF (5 mL) and treated with γ-azidobutyric acid (0.201 g, 1.55 mmol, 1.3 equiv), triethylamine (025 mL, 1.76 mmol, 1.5 equiv) and HATU (0.489 g, 1.29 mmol, 1.1 equiv). After 1 h at room temperature, the reaction mixture was diluted with toluene (30 mL) and evaporated. Co-evaporation with toluene (3×30 ml) resulted in a dark oil. The product was purified by flash chromatography (15 g SiO$_2$; DCM, then DCM/MeOH 90:10, then DCM/MeOH 80:20). The product containing fractions were further purified by reversed phase C-18 chromatography (water/acetonitrile 75:25, then 70:30, 65:35, 60:40, 55:45, 50:50) to give 14 (0.94 g, 62%).

10. Synthesis of (S)-1-azido-4,20,23,26-tetraoxo-21-(4-(6-(6-(6-(2-(propan-2-ylidene)hydrazinyl)nicotinamido)hexanamido) hexanamido)butyl)-9,12,15-trioxa-5,19,22,27-tetraaza-tritriacontan-33-oic acid (15)

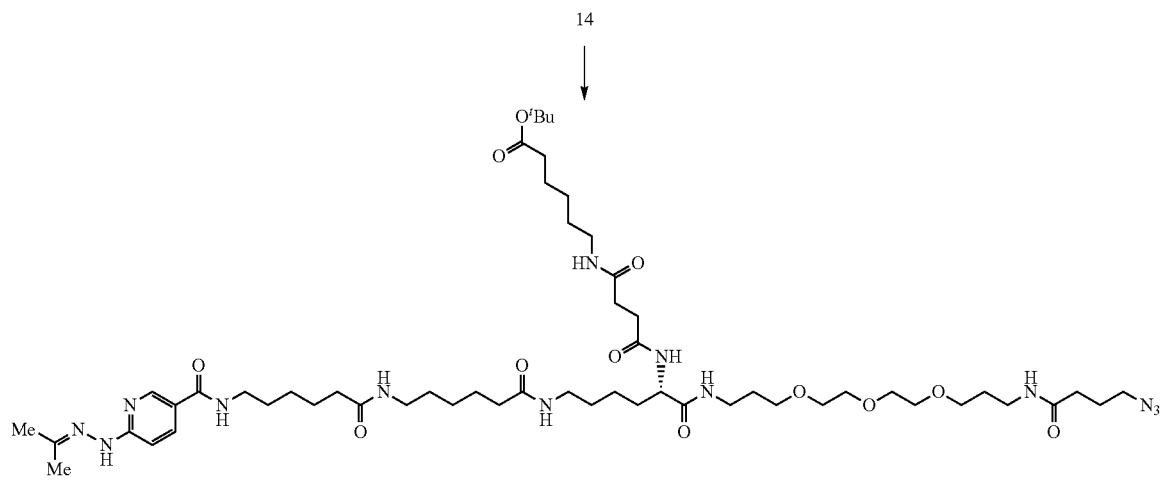

An aq. 6 M HCl solution (10 mL) was added to 14 (0.85 g, 0.71 mmol) and the solution was stirred at room temperature. After 20 min, the clear solution was cooled in an ice-bath, an aq. 2 M NaOH solution (31 mL, previously titrated against HCl solution) was added and the neutralized solution was lyophilized. The residue was suspended in MeOH/acetone 1:1 (50 ml) and the volatiles were evaporated under reduced pressure at 40° C. This procedure was repeated 2 more times. Then, the suspension was filtered, the solids were washed with MeOH/acetone 1:1 (100 ml) and the filtrate was evaporated. The product was purified by reversed phase C-18 chromatography (water/acetone/triethylamine 90:10:1, then water/acetone/acetonitrile 85:10:5) to give 15 (0.39 g, 51%) as light-grey solid foam.

11. Synthesis of HATRIC (16)

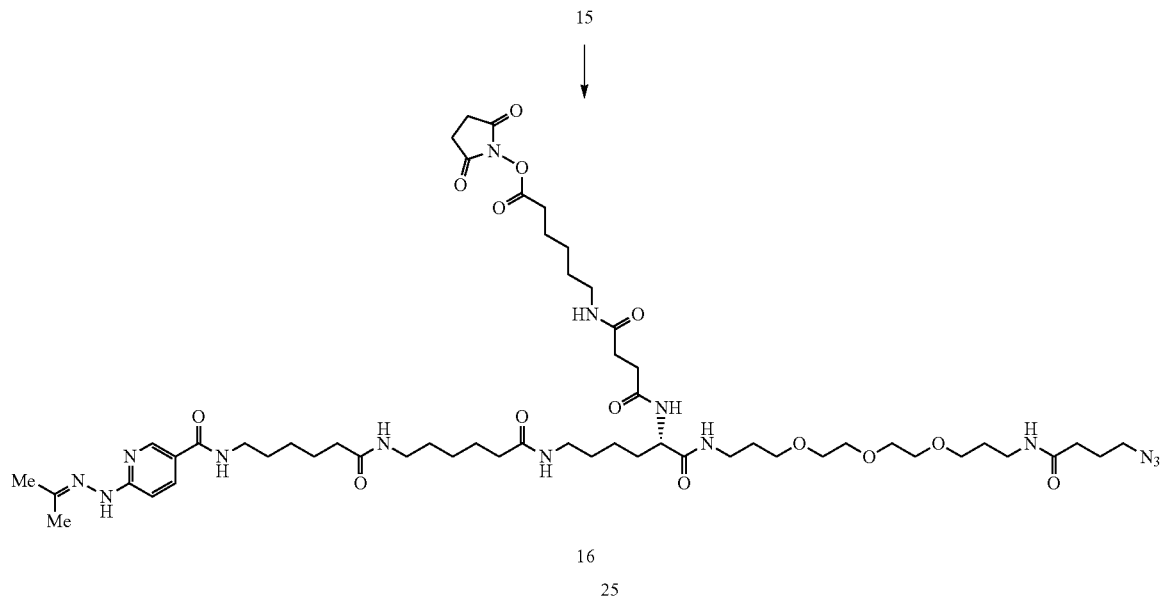

16

A suspension of 15 (300 mg, 0.28 mmol) in DMF (15 mL) was treated with Hünig's base (100 μL, 0.56 mmol, 2.0 equiv), N-hydroxysuccinimide (65 mg, 0.56 mmol, 2.0 equiv) and N,N'-disuccinimidyl carbonate (143 mg, 0.56 mmol, 2.0 equiv) and then stirred at 40° C. for 90 min. Then the reaction mixture was treated with toluene (50 ml) and evaporated. Co-evaporation with toluene (3×50 ml) resulted in an oil, which was dried in vacuo. The product was purified by size exclusion chromatography using sephadex LH-20 (DCM/acetone/MeOH 8:1:1) to give 16 (295 mg, 90%) as an orange solid.

$^1$H-NMR (600 MHz, DMSO-$d_6$) δ=9.62 (br, 1H), 8.57 (dd, J=2.4, 0.8 Hz, 1H), 8.25 (t, J=5.6 Hz, 1H), 7.99 (dd, J=8.8, 2.4 Hz, 1H), 7.95 (d, J=8.0 Hz, 1H), 7.87-7.77 (m, 3H), 7.71 (t, J=5.6 Hz, 2H), 7.04 (dd, J=8.8, 0.8 Hz, 1H), 4.12-4.05 (m, 1H), 3.52-3.49 (m, 4H), 3.48-3.43 (m, 4H), 3.40-3.35 (m, 4H), 3.32-3.28 (m, 2H), 3.21 (q, J=7.2, 5.7 Hz, 2H), 3.09-3.04 (m, 4H), 3.03-2.96 (m, 6H), 2.83-2.78 (m, 4H), 2.65 (t, J=7.3 Hz, 2H), 2.39-2.26 (m, 4H), 2.13 (t, J=7.4 Hz, 2H), 2.06-2.00 (m, 4H), 1.96 (s, 3H), 1.93 (s, 3H), 1.73 (dq, J=7.8, 6.9 Hz, 2H), 1.66-1.57 (m, 7H), 1.54-1.43 (m, 7H), 1.43-1.29 (m, 6H), 1.29-1.13 (m, 8H)

$^{13}$C-NMR (151 MHz, DMSO-$d_6$) δ=171.81, 171.80, 171.62, 171.60, 171.4, 171.0, 170.2, 168.9, 164.8, 159.3, 148.5, 147.7, 136.7, 120.6, 105.1, 69.8, 69.7, 69.5 (2 carbon), 68.1, 68.0, 52.6, 50.3, 38.9, 38.29, 38.25, 38.2, 35.9, 35.8, 35.4, 32.2, 31.5, 30.73, 30.71, 30.7, 30.1, 29.3, 29.2, 29.1, 29.0, 28.9, 28.6, 26.20, 26.15, 25.43, 25.42, 25.14, 25.13, 25.1, 24.5, 23.9, 23.0, 17.0

IR (neat, $v_{max}$/cm$^{-1}$) 3287, 2930, 2858, 2099, 1738, 1631, 1603, 1538, 1364, 1256, 1206, 1121, 1068, 712, 644

ESI-MS: calc. for $C_{55}H_{90}N_{14}NaO_{14}$ [M+Na$^+$] 1193.6653; found 1193.6668 [α]$^{25}_D$=−4.0 (c=0.2, MeOH)

EXAMPLE 2

Ligand-Based Receptor Capturing with Epidermal Growth Factor Conjugated to HATRIC (Obtained from Example 1) on H358 Bronchiole Cells at pH 7.4

In the sample reaction, 300 μg EGF were coupled to 70 μg tri-functional cross-linker HATRIC (obtained from Example 1). In the control reaction, the ligand-reactive functionality of 70 ug HATRIC was quenched with an equimolar amount of glycine. This procedure corresponds to step (i). 3 replicates were prepared for treatment with the glycine-quenched HATRIC and 3 replicates were prepared for treatment with EGF-quenched HATRIC. Preparation means that for each of the 6 samples, 15 million cells of H358 bronchiole cell line were oxidized with 1.5 mM NaIO$_4$ for 15 min, pH6.5, 4° C. to generate aldehydes on carbohydrate structures of cell surface glycoproteins according to steps (i) and (ii). The oxidized cells were incubated with the EGF-conjugated or glycine-quenched HATRIC in the presence of 5 mM 2-amino-5-methoxybenzoic acid (XX) for 90 min at pH 7.4, 4° C. as described in step (iv b). Subsequently, cells were lysed by sonication in 8M Urea, 0.1% Rapigest containing protease inhibitors according to step (v). HATRIC-tagged full sequence glycoproteins were captured with alkyne agarose beads in a copper-catalyzed alkyne-azide cycloaddition reaction (1 mM CuSO$_4$, 6.25 mM THPTA and 2 mM sodium ascorbate for 18 hrs at room temperature). Upon reduction and alkylation of proteins, unbound proteins were removed by washing agarose matrix with 1% SDS, 8M Urea, 5M NaCl, 100 mM NaHCO$_3$, pH 11, 100 mM NH$_4$HCO$_3$ and 20% Acetonitrile. This summarizes step (vi) of the procedure. Finally, the peptides of cell surface glycoproteins were released by tryptic digestion for 16 h at 37° C. Upon desalting, peptides were subjected to MS/MS analysis. Resulting mass spectrometric data were quantified relatively based on MS1-peak intensities. This outlines step (vii) and (ix) of the procedure. Briefly, the abundances of identified peptides were summed up for each glycoprotein receptor throughout the replicates and pairwise compared to the abundance in the replicates of the control reaction. This comparison was tested for statistical significance to report p-values. P-values were adjusted for multiple comparisons using Benjamini-Hochberg method that controls the experiment-wide false-discovery rate (FDR). A glycoprotein target receptor candidate is defined as a receptor with an FDR-adjusted p-value of less than or equal to 0.001 and an enrichment factor in the ligand sample of fourfold or greater. Epidermal growth factor receptor (EGFR) was identified in the upper right target box as the glycoprotein target receptor for EGF. This finding corresponds to previously published findings and demonstrates the usefulness of the approach.

EXAMPLE 3

Synthesis of Crosslinker "TRICEPS 4.0"

1. Synthesis of TRICEPS Intermediate

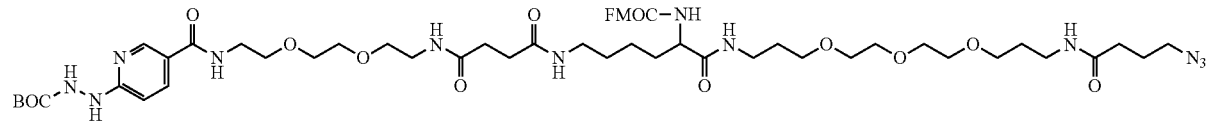

The title compound is obtained in anlogy to the procedure described in example 1, using the respective starting materials.

2. Synthesis of TRICEPS 4.0

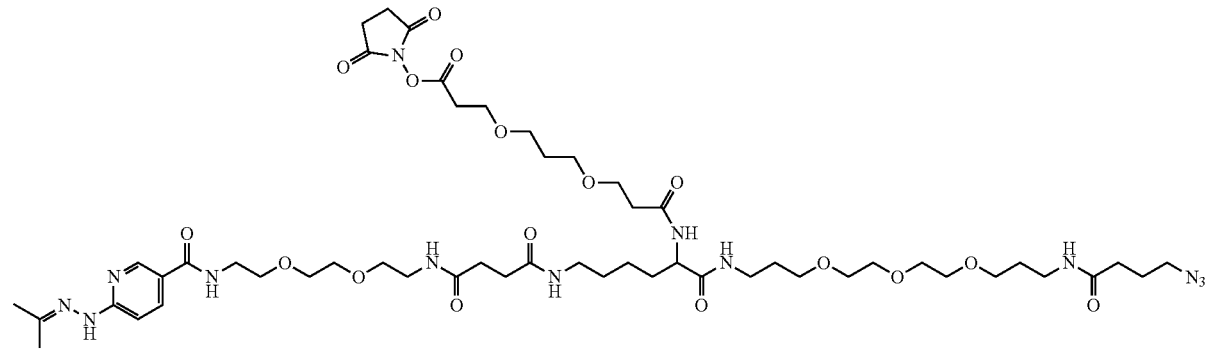

The title compound is obtained in analogy to the procedure described in example 1, using the compound of ex. 3.1 and the respective starting materials.

EXAMPLE 4

Synthesis of Crosslinker "TRICEPS 5.0"

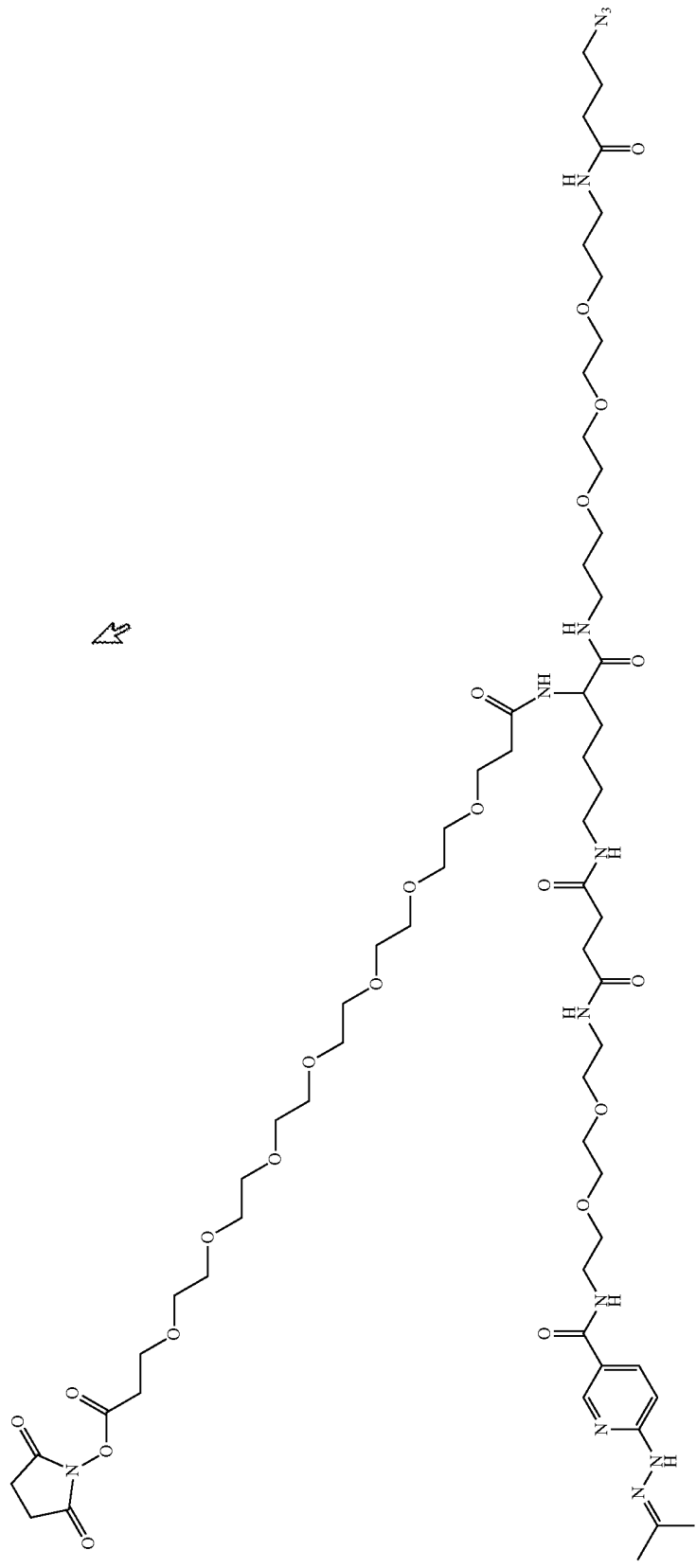

The title compound is obtained in analogy to the procedure described in example 1, using the compound of ex. 3.1 and the respective starting materials.

The invention claimed is:

1. A compound of formula (Ib)

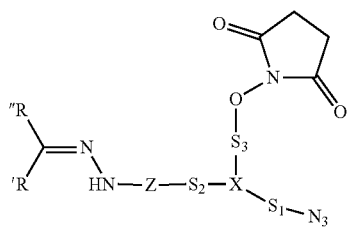

wherein

X represents a core structure;

S₁, S₂, S₃ represents independently of each other a spacer group;

Z represents an unsubstituted pyridyl;

R' represents methyl; and

R" represents methyl;

wherein

X represents a group of formula (I-I)

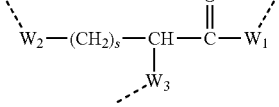

wherein the dotted lines represent the linkage of $W_1$, $W_2$, $W_3$ to groups $S_1$, $S_2$, $S_3$, and s represents 4, $W_1$ represents —NH—, $W_2$ represents —CONH—, $W_3$ represents —NHCO—;

$S_1$ represents $C_{(1-24)}$alkylene;

$S_2$ represents $C_{(1-24)}$alkylene;

$S_3$ represents $C_{(1-24)}$alkylene;

wherein said alkylene being a straight-chain, wherein said alkylene being substituted or unsubstituted, wherein one or more, non-adjacent; —CH₂— groups of said alkylene may independently from each other be replaced by one or more bridging groups Y; with the proviso that heteroatoms, such as O and N, are not directly linked to each other, and wherein Y represents a group —NR₁—CO—, —CO—NR₁—; and R₁ represents H.

2. The compound according to claim 1, wherein the compound is of the formula (Ic)

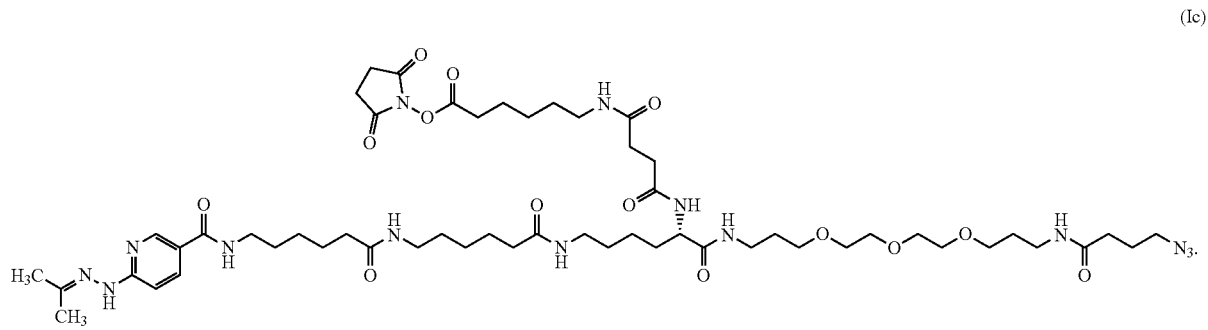 [SMILES: CC(C)=NNc1ccc(C(=O)NCCCCCC(=O)NCCCCCC(=O)NCCCC[C@H](NC(=O)CCC(=O)NCCCCCC(=O)ON2C(=O)CCC2=O)C(=O)NCCCOCCOCCOCCCNC(=O)CCCN=[N+]=[N-])cn1]

3. A method of characterizing and analyzing interactions between a ligand and a target glycoprotein receptor comprising:

using one of a compound of formula (Ib), or a compound of formula (Ic):

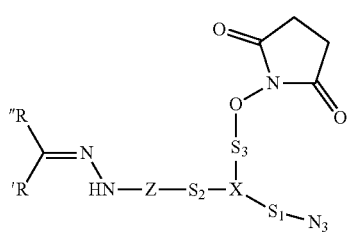

(Ic)

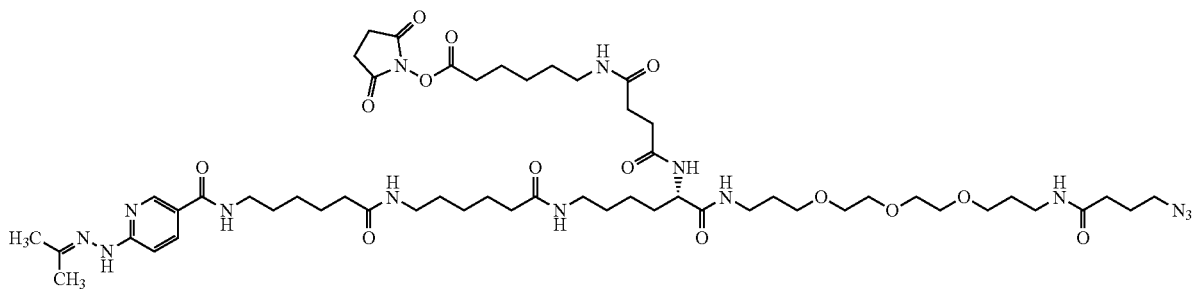

wherein
X represents a core structure;
$S_1$, $S_2$, $S_3$ represents independently of each other a spacer group;
Z represents unsubstituted pyridyl;
R' represents methyl; and
R" represents methyl;
wherein
X represents a group of formula (I-I)

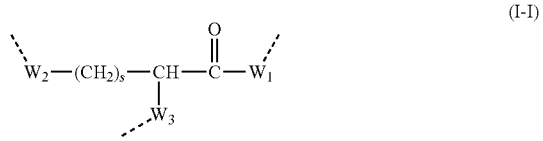

wherein the dotted lines represent the linkage of $W_1$, $W_2$, $W_3$ to groups $S_1$, $S_2$, $S_3$, and
s represents 4,
$W_1$ represents —NH—,
$W_2$ represents —CONH—,
$W_3$ represents —NHCO—;
$S_1$ represents $C_{(1-24)}$alkylene;
$S_2$ represents $C_{(1-24)}$alkylene;
$S_3$ represents $C_{(1-24)}$alkylene;
wherein the alkylene being a straight-chain,
wherein the alkylene being substituted or unsubstituted,
wherein one or more, non-adjacent, —$CH_2$— groups of said alkylene may independently from each other be replaced by one or more bridging groups Y; with the proviso that heteroatoms, such as O and N, are not directly linked to each other, and wherein
Y represents a group —O—, —$NR_1$—CO—, —CO—$NR_1$—; and
$R_1$ represents H;
using a ligand;
using a target glycoprotein receptor; and
characterizing and analyzing interactions between the ligand and the target.

4. The method according to claim 3, further comprising:
selecting the target glycoprotein receptor from cell surface receptor and a secreted glycoprotein receptor; and/or
selecting the ligand to be an orphan ligand selected from the group consisting of proteins, peptides, small molecules and viruses.

5. A method of identifying specific interactions between a ligand (II) and a target (III) in a sample, wherein
the target (III) is a glycoprotein receptor; and
the ligand (II) recognizes a ligand-specific domain on the target (III);

wherein
a target-ligand-reagent-complex (VI) is formed, said complex (VI) comprising
a compound of formula (Ib) according to claim 1,
a ligand (II) and
a target (III),
wherein
ligand (II) is covalently bound to the N-hydroxysuccinimide activated functional group present in formula (Ib), and target (III) is covalently bound to the hydrazone-group present in formula (Ib), or
ligand (II) is covalently bound to the hydroxysuccinimide ester present in formula (Ic), and
target (III) is covalently bound to the hydrazone-group present in formula (Ic).

6. The method of claim 5, said method comprising the steps of:
i) providing a sample comprising said target (III),
ii) subjecting the target (III) to oxidative treatment to generate aldehyde functions on at least one carbohydrate residue thereby obtaining an oxidized target (IV),
iii) providing a tri-functional crosslinking reagent of formula (Ib) according to claim 1, and allowing the N-hydroxysuccinimide activated functional group thereof to conjugate to said ligand (II) to obtain a ligand-reagent-complex (V), or providing a or a tri-functional crosslinking reagent of formula (Ic) according to claim 2, and allowing the hydroxysuccinimide ester group thereof to conjugate to said ligand (II) to obtain a ligand-reagent-complex (V),
iv) contacting the sample of step (ii) with complex (V) of step (iii) under conditions under which (a) the complex (V) is able to bind the ligand-specific domain on the oxidized target (IV) and (b) the hydrazone group (R'R"C=N—NH—) of said complex (V) is converted to its free form and allowed to covalently bind the oxidized carbohydrate target (IV), to obtain a target-ligand-reagent complex (VI) comprising a covalently bound ligand and a covalently bound target,
v) lysing the sample of step (iv) to make membrane-embedded cell surface proteins and said complex (VI) available and react with matrix (VII), to obtain a matrix-bound complex (VIII),
vi) enriching said complex from the sample by using an affinity matrix (VII) to obtain a matrix-bound complex (VIII),
vii) digesting said matrix-bound complex (VIII) to obtain (a) released peptides (IX) and (b) glycopeptides bound on a matrix (X), viii) optionally releasing of bound glycopeptides (X) from said matrix (VIII) to obtain released glycopeptides (XI)
ix) analyzing and quantifying the released peptides (IX), (XI), and
x) identifying the interactions between the ligand and the target glycoprotein receptor.

7. The method according to claim 5, wherein the target (III) is either in solution or on the surface of a cell.

8. The method according to claim 6,
wherein in step (iv)
the reaction conditions of (a) are pH 6.5-7.4; temperature is 0-10° C.; 10-240 min;
the reaction conditions of step (b) include providing of an effective amount of a catalyst (XX) selected from the group of amino-benzoic acids at pH 6.5-7.4;
wherein in step (v) the dual-bound target-ligand-reagent complex (VI) and random glycoprotein-reagent complexes are released from the sample by lysis of cells and membranes;
wherein in step (vi) purification is achieved using a protein-compatible buffers containing 1% sodium dodecyl sulfate, 8M urea, 20% acetonitrile, 5M sodium chloride, 80% isopropanol and 100 mM sodium bicarbonate and having a pH of 11.

9. The method according to claim 5, wherein the compound is of formula (Ib)

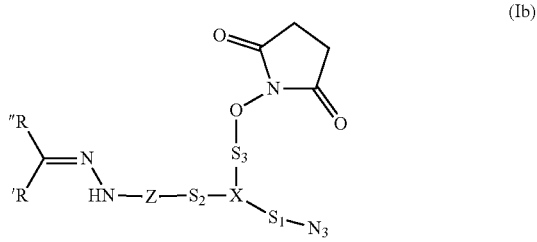

(Ib)

wherein the substituents are as defined in claim 1.

10. The method according to claim 5, wherein the compound is of formula (Ic)

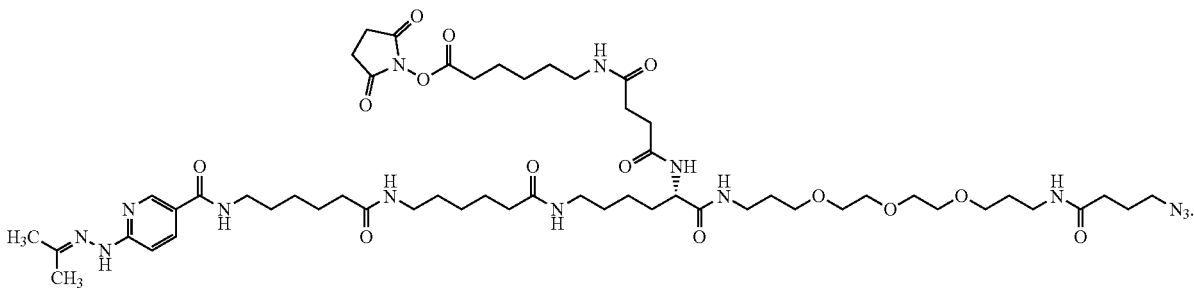

(Ic)

11. The method according to claim 6, wherein at step ix) the released peptides (IX), (XI) are analyzed and quantified by high mass accuracy mass spectroscopy and/or at step x) interactions between the ligand and the target glycoprotein receptor are identified through quantitative comparison to a control reaction.

12. The method according to claim 3, wherein the compound of formula (Ic) is used.

* * * * *